(12) United States Patent
Brewer et al.

(10) Patent No.: US 8,148,360 B2
(45) Date of Patent: Apr. 3, 2012

(54) SUPRAMOLECULAR METALLIC COMPLEXES EXHIBITING BOTH DNA BINDING AND PHOTOCLEAVAGE

(75) Inventors: Karen J. Brewer, Blacksburg, VA (US); Brenda Winkel, Blacksburg, VA (US)

(73) Assignee: Virginia Tech Intellectual Properties, Inc., Blacksburg, VA (US)

( * ) Notice: Subject to any disclaimer, the term of this patent is extended or adjusted under 35 U.S.C. 154(b) by 849 days.

(21) Appl. No.: 11/851,689

(22) Filed: Sep. 7, 2007

(65) Prior Publication Data

US 2008/0113954 A1 May 15, 2008

Related U.S. Application Data

(60) Provisional application No. 60/824,802, filed on Sep. 7, 2006.

(51) Int. Cl.
*A61K 31/555* (2006.01)
*C07F 15/00* (2006.01)

(52) U.S. Cl. ......... 514/186; 544/225; 514/185; 514/188

(58) Field of Classification Search .................. 514/186, 514/188; 544/225; 435/6
See application file for complete search history.

(56) References Cited

U.S. PATENT DOCUMENTS

| | | | | |
|---|---|---|---|---|
| 6,962,910 B2 * | 11/2005 | Brewer et al. | .................. | 514/188 |
| 7,122,171 B2 * | 10/2006 | Brewer et al. | .................. | 423/657 |
| 7,582,584 B2 * | 9/2009 | Brewer et al. | .................. | 502/150 |
| 7,612,057 B2 * | 11/2009 | Brewer et al. | .................. | 514/188 |
| 2003/0180767 A1 * | 9/2003 | Brewer et al. | ...................... | 435/6 |

* cited by examiner

*Primary Examiner* — Charanjit Aulakh
(74) *Attorney, Agent, or Firm* — Whitham Curtis Christofferson & Cook, PC

(57) ABSTRACT

Supramolecular complexes that target and cleave DNA are provided. The supramolecular complexes include at least one metal-to-ligand charge transfer (MLCT) light absorbing unit, at least one Pt based DNA binding unit, and at least one bridging unit that serves to connect the components. The Pt-based DNA binding unit binds the complex to DNA, and the MLCT unit absorbs light, thereby sensitizing molecular oxygen to produce reactive oxygen species in close proximity to the complex and the bound DNA. The reactive oxygen species cleave the bound DNA.

37 Claims, 10 Drawing Sheets

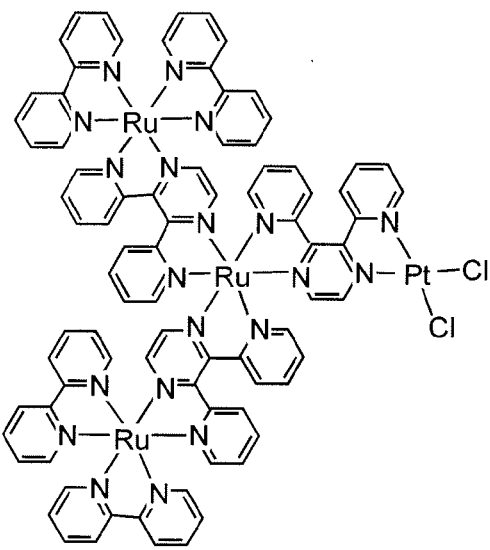
[{(bpy)₂Ru(dpp)}₂Ru(dpp)PtCl₂](PF₆)₆
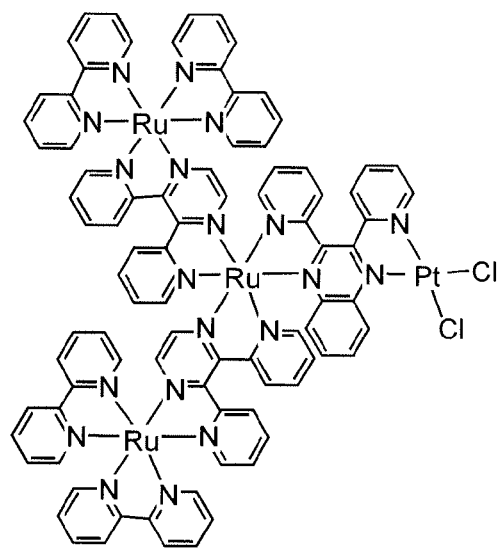
[{(bpy)₂Ru(dpp)}₂Ru(dpq)PtCl₂](PF₆)₆
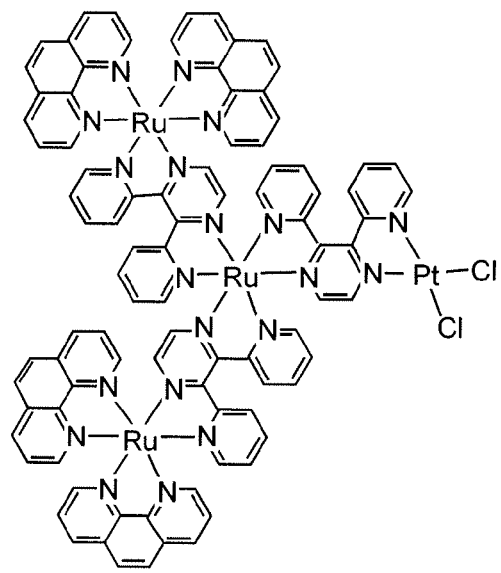
[{(phen)₂Ru(dpp)}₂Ru(dpp)PtCl₂](PF₆)₆
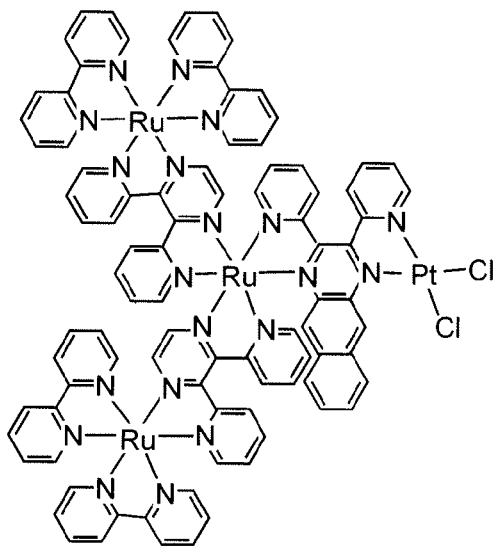
[{(bpy)₂Ru(dpp)}₂Ru(dpb)PtCl₂](PF₆)₆
*Figure 4*

US 8,148,360 B2

SUPRAMOLECULAR METALLIC COMPLEXES EXHIBITING BOTH DNA BINDING AND PHOTOCLEAVAGE

CROSS-REFERENCE TO RELATED APPLICATIONS

This application claims priority to U.S. Provisional Patent Application 60/824,802 filed Sep. 7, 2006, and the complete contents thereof is herein incorporated by reference.

This invention was made using funds from grants from the National Science Foundation having grant number CHE-0408445. The United States government may have certain rights in this invention.

BACKGROUND OF THE INVENTION

1. Field of the Invention

The invention generally relates to supramolecular complexes that target and cleave DNA. In particular, the invention provides supramolecular complexes that include at least one metal-to-ligand charge transfer (MLCT) light absorbing unit, at least one Pt based DNA binding unit, and at least one bridging unit that serves to connect the components.

2. Background of the Invention

In the treatment of diseases related to hyperproliferating tissue such as cancer and non-malignant lesions, photochemical approaches are of particular interest. Photodynamic therapy (PDT), which utilizes photochemical reagents capable of cleaving DNA provides reaction control and can be highly targeted, thereby minimizing damage to healthy tissue.

Some progress has been made in this area. For example, U.S. Pat. No. 6,962,910 to Brewer et al. describes a method for cleaving DNA using supramolecular complexes. The supramolecular complexes described by Brewer et al. include one or more metal-to-ligand charge transfer (MLCT) light absorbing units, an electron acceptor, and at least one bridging unit that serves to connect the components.

However, there remains an ongoing need to develop new types of photochemical reagents that are capable of being targeted, and which efficaciously bind to and cleave DNA, especially in hyperproliferating cells.

SUMMARY OF THE INVENTION

A new genre of supramolecular complexes has been prepared and characterized. The new systems are multifunctional complexes that bind to DNA through a platinum site (analogous to cisplatin) and then photocleave DNA using a MLCT light absorber that sensitizes molecular oxygen to generate a reactive oxygen species. The reactive oxygen species is therefore responsible for DNA cleavage. This is known as an indirect DNA photocleavage mechanism. The presence of a Pt moiety in the complex results in the targeted delivery of the complex to DNA, thereby enhancing the efficiency of DNA cleavage by the complexes.

It is an object of this invention provide a supramolecular complex comprising 1) at least one metal to ligand charge transfer (MLCT) light absorbing metal, 2) at least one bridging ligand, and 3) at least one Pt based DNA binding unit. In one embodiment, the at least one metal to ligand charge transfer (MLCT) light absorbing metal is selected from ruthenium(II), osmium(III), rhenium(I), iron(II) and platinum(II). The at least one bridging ligand may be a π-acceptor ligand; in some embodiments, the at least one bridging ligand is selected from 2,3-bis (2-pyridyl)pyrazine; 2,2'-bipyridimidine; 2,3-bis(2-pyridyl)quinoxaline; and 2,3,5,6,-tetrakis(2-pyridyl)pyrazine. The at least one Pt based DNA binding unit may be a Pt with at least one labile ligand, for example, cis-PtCl$_2$. The supramolecular complex may further comprise at least one terminal ligand, which, in some embodiments, is a π-acceptor ligand. In some embodiments, the at least one terminal ligand is 2,2'-bipyridine; 2,2':6',2"-terpyridine; triphenylphosphine; and 2,2'-phenylpyridine or diethylphenylphosphine. In a preferred embodiments of the invention, the light to which the complex is exposed is visible light. Exemplary supramolecular complexes include but are not limited to [{(bpy)$_2$Ru(dpp)}$_2$Ru(dpp)PtCl$_2$](PF$_6$)$_6$, [{(bpy)$_2$Ru(dpp)}$_2$Ru(dpq)PtCl$_2$](PF$_6$)$_6$, [{(bpy)$_2$Ru(dpp)}$_2$Ru(dpb)PtCl$_2$](PF$_6$)$_6$, [{(phen)$_2$Ru(dpp)}$_2$Ru(dpp)PtCl$_2$](PF$_6$)$_6$ and [{(bpy)$_2$Os(dpp)}$_2$Ru(dpq)PtCl$_2$](PF$_6$)$_6$.

The invention further provides a method for cleaving DNA. The method comprises the steps of a) combining said DNA with a supramolecular complex comprising 1) at least one metal to ligand charge transfer (MLCT) light absorbing metal, 2) at least one bridging ligand, and 3) at least one Pt based DNA binding unit, the combining being carried out in the presence of molecular oxygen and under conditions that allow the at least one Pt based DNA binding unit to bind to DNA; and b) exposing the DNA to light or radiant energy in a quantity sufficient to cause sensitization of the molecular oxygen by the MLCT light absorbing metal, thereby forming a reactive oxygen species that cleaves the DNA. In some embodiments, the at least one metal to ligand charge transfer (MLCT) light absorbing metal is ruthenium(II), osmium(III), rhenium(I), iron(II) or platinum(II). In another embodiments, the at least one bridging ligand is a π-acceptor ligand. The at least one bridging ligand may be, for example, 2,3-bis(2-pyridyl)pyrazine; 2,2'-bipyridimidine; 2,3-bis(2-pyridyl)quinoxaline; or 2,3,5,6,-tetrakis(2-pyridyl)pyrazine. In one embodiment, the at least one Pt based DNA binding unit is a Pt with at least one labile ligand, for example, cis-PtCl$_2$. The supramolecular complex may further comprise at least one terminal ligand, which, in some embodiments, is a π-acceptor ligand. In some embodiments, the at least one terminal ligand is 2,2'-bipyridine; 2,2':6',2"-terpyridine; triphenylphosphine; and 2,2'-phenylpyridine or diethylphenylphosphine. In a preferred embodiments of the invention, the light to which the complex is exposed is visible light. Exemplary supramolecular complexes include but are not limited to [{(bpy)$_2$Ru(dpp)}$_2$Ru(dpp)PtCl$_2$](PF$_6$)$_6$, [{(bpy)$_2$Ru(dpp)}$_2$Ru(dpq)PtCl$_2$](PF$_6$)$_6$, [{(bpy)$_2$Ru(dpp)}$_2$Ru(dpb)PtCl$_2$](PF$_6$)$_6$, [{(phen)$_2$Ru(dpp)}$_2$Ru(dpp)PtCl$_2$](PF$_6$)$_6$, and [{(bpy)$_2$Os(dpp)}$_2$Ru(dpq)PtCl$_2$](PF$_6$)$_6$. In one embodiment of the method, the combining step occurs within a hyperproliferating cell.

The invention further provides a composition for effecting the cleavage of DNA in hyperproliferating cells. The composition comprises a) a supramolecular complex comprising 1) at least one metal to ligand charge transfer (MLCT) light absorbing metal, 2) at least one bridging ligand, and 3) at least one Pt based DNA binding unit, the combining being carried out in the presence of molecular oxygen and under conditions that allow the at least one Pt based DNA binding unit to bind to DNA; and b) a carrier. In one embodiment, the at least one metal to ligand charge transfer (MLCT) light absorbing metal is selected from ruthenium(II), osmium(III), rhenium(I), iron (II) and platinum(II). The at least one bridging ligand may be a π-acceptor ligand; in some embodiments, the at least one bridging ligand is selected from 2,3-bis(2-pyridyl)pyrazine; 2,2'-bipyridimidine; 2,3-bis(2-pyridyl)quinoxaline; and 2,3,5,6,-tetrakis(2-pyridyl)pyrazine. The at least one Pt based DNA binding unit may be a Pt with at least one labile ligand, for example, cis-PtCl$_2$. The supramolecular complex may further comprise at least one terminal ligand, which, in some embodiments, is a π-acceptor ligand. In some embodiments, the at least one terminal ligand is 2,2'-bipyridine; 2,2':6',2"-terpyridine; triphenylphosphine; and 2,2'-phenylpyridine or diethylphenylphosphine. In a preferred embodiments of the invention, the light to which the complex is exposed is visible light. Exemplary supramolecular complexes include but are not limited to [{(bpy)$_2$Ru(dpp)}$_2$Ru(dpp)PtCl$_2$](PF$_6$)$_6$, [{(bpy)$_2$Ru(dpp)}$_2$Ru(dpq)PtCl$_2$](PF$_6$)$_6$, [{(bpy)$_2$Ru(dpp)}$_2$Ru(dpb)PtCl$_2$](PF$_6$)$_6$, [{(phen)$_2$Ru(dpp)}$_2$Ru(dpp)PtCl$_2$](PF$_6$)$_6$, and [{(bpy)$_2$Os(dpp)}$_2$Ru(dpq)PtCl$_2$](PF$_6$)$_6$. The supramolecular complex may be dissolved or dispersed in the carrier.

The invention also provides a method for decreasing the replication of hyperproliferating cells. The method comprises the steps of a) delivering to said cells a supramolecular complex comprising 1) at least one metal to ligand charge transfer (MLCT) light absorbing metal, 2) at least one bridging ligand, and 3) at least one Pt based DNA binding unit; and 2) applying light or radiant energy to the hyperproliferating cells. The step of applying light to the hyperproliferating cells induces sensitization of the molecular oxygen by the MLCT light absorbing metal, thereby forming a reactive oxygen species that cleaves the DNA of the hyperproliferating cells, thereby causing a decrease in the replication of the hyperproliferating cells. In some embodiments, the at least one metal to ligand charge transfer (MLCT) light absorbing metal is ruthenium(II), osmium(III), rhenium(I), iron(II) or platinum (II). In another embodiments, the at least one bridging ligand is a π-acceptor ligand. The at least one bridging ligand may be, for example, 2,3-bis(2-pyridyl)pyrazine; 2,2'-bipyridimidine; 2,3-bis(2-pyridyl)quinoxaline; or 2,3,5,6,-tetrakis(2-pyridyl)pyrazine. In one embodiment, the at least one Pt based DNA binding unit is a Pt with at least one labile ligand, for example, cis-PtCl$_2$. The supramolecular complex may further comprise at least one terminal ligand, which, in some embodiments, is a π-acceptor ligand. In some embodiments, the at least one terminal ligand is 2,2'-bipyridine; 2,2':6',2"-terpyridine; triphenylphosphine; and 2,2'-phenylpyridine or diethylphenylphosphine. In a preferred embodiments of the invention, the light to which the complex is exposed is visible light. Exemplary supramolecular complexes include but are not limited to [{(bpy)$_2$Ru(dpp)}$_2$Ru(dpp)PtCl$_2$](PF$_6$)$_6$, [{(bpy)$_2$Ru(dpp)}$_2$Ru(dpq)PtCl$_2$](PF$_6$)$_6$, [{(bpy)$_2$Ru(dpp)}$_2$Ru(dpb)PtCl$_2$](PF$_6$)$_6$, [{(phen)$_2$Ru(dpp)}$_2$Ru(dpp)PtCl$_2$](PF$_6$)$_6$, and [{(bpy)$_2$Os(dpp)}$_2$Ru(dpq)PtCl$_2$](PF$_6$)$_6$. In a preferred embodiment, the light to which the complex is exposed is visible light. In some embodiments, the hyperproliferating cells are cancer cells.

In addition, the supramolecular complex of the invention may further comprise a counterion, examples of which include PF$_6^-$, Cl$^-$, Br$^-$, I$^-$, CF$_3$SO$_3^-$, BF$_4^-$, NO$_3^-$, CLO$_4^-$, CO$_3^{-2}$, and

BRIEF DESCRIPTION OF THE DRAWINGS

FIG. 4. Additional exemplary supramolecular complexes.

DETAILED DESCRIPTION OF THE PREFERRED EMBODIMENTS OF THE INVENTION

The present invention provides multifunctional supramolecular assemblies that are capable of both binding to and cleaving DNA. DNA binding is carried out through a Pt-based DNA binding moiety or unit, and photocleavage of the bound DNA is carried out as a result of the presence of an MLCT light absorbing moiety or unit. The MLCT unit mediates cleavage of the bound DNA by sensitizing molecular oxygen to generate a reactive oxygen species, and it is the reactive oxygen species that is responsible for DNA cleavage. In other words, the complexes of the present invention cleave DNA via an indirect DNA photocleavage mechanism. $^3$MLCT excited states of the light absorbers can cause direct DNA cleavage via base oxidation or indirect cleavage via energy or electron transfer to molecular oxygen. In the present invention, indirect cleavage via an oxygen mediated pathway is operative.

Figure 1:
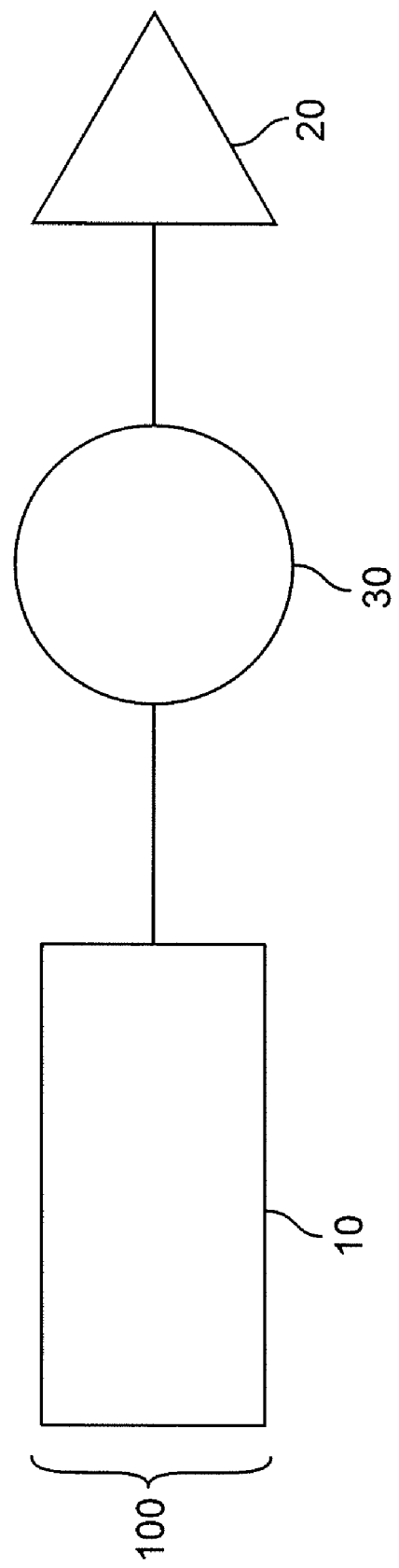
FIG. 1. Schematic representation of the supramolecular complex of the invention.
Figure 2:
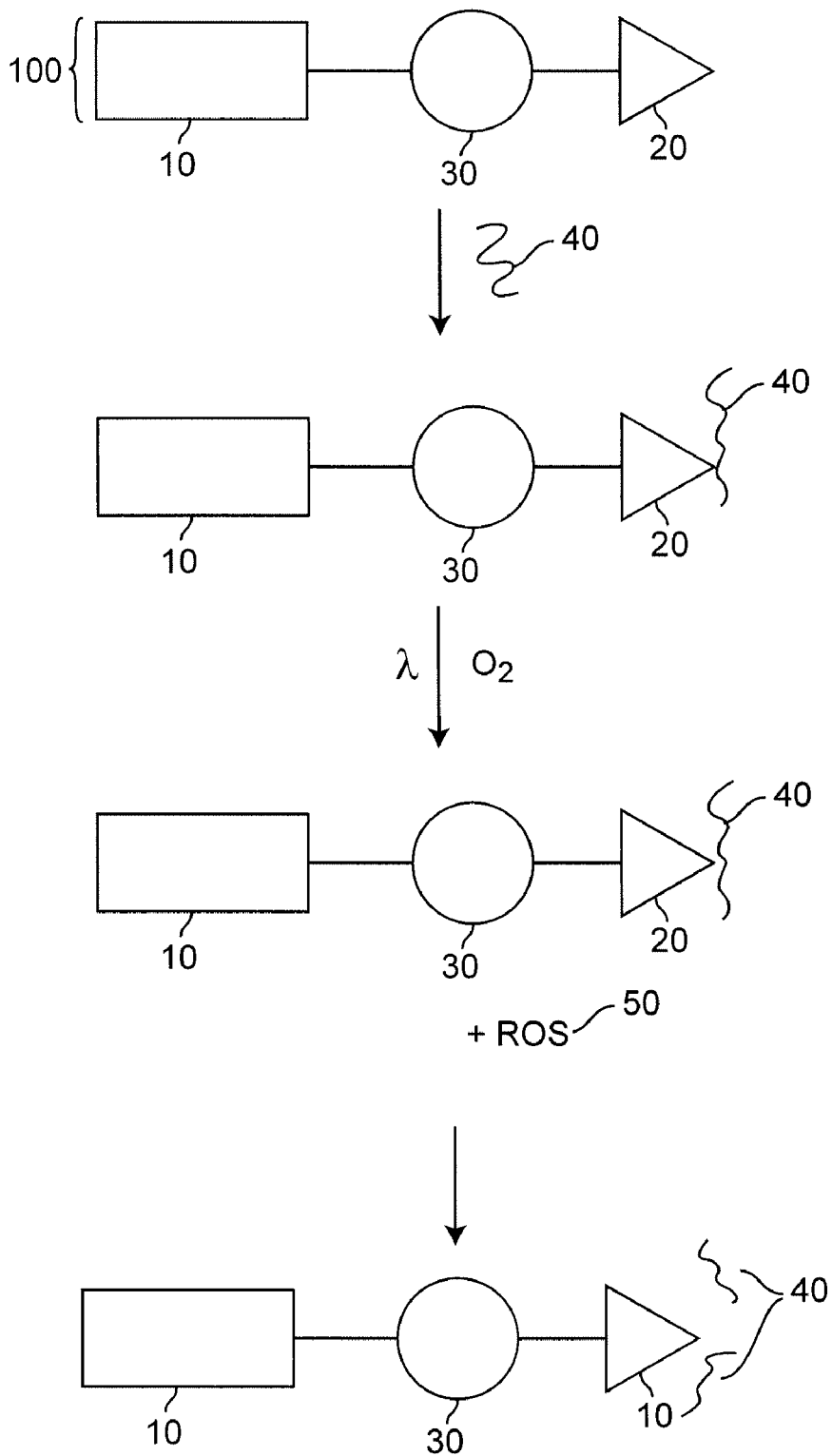
FIG. 2. Schematic representation of the DNA cleaving reaction of the supramolecular complex of the invention.

The components of the new supramolecular assembly are 1) at least one MLCT light absorber (for example, a Ru polypyridine chromophore); 2) at least one Pt-based DNA binding unit (e.g cisplatin, cis-PtCl$_2$); and 3) at least one bridging unit that serves to connect the components. The bridging unit may be, for example, a π acceptor ligand. The assembly is illustrated schematically in FIG. 1, where a supramolecular assembly 100 is depicted in which 10 represents one or more MLCT units, 20 represents one or more Pt-based DNA binding units, and 30 represents one or more bridging units. In the functioning of this system, Pt-based DNA binding unit 20 binds the supramolecular assembly to DNA, whereupon MLCT unit 10 absorbs light and thereby mediates the conversion of ambient molecular oxygen to form a reactive oxygen species. The presence of a platinum DNA binding moiety in the complex provides a means of targeting the complex to DNA, thereby enhancing delivery of the macromolecular complex to the intended site of activity. Due to the presence of the Pt-based DNA binding unit 20 in the complex, the reactive oxygen species is generated in close proximity to the bound DNA, facilitating the ability of the reactive oxygen species to cleave the DNA. The functioning of the system is illustrated schematically in FIG. 2, which shows the supramolecular complex 100 binding to DNA 40 via Pt-based DNA binding unit 20. In the presence of light (λ) and molecular oxygen ($O_2$), MLCT unit 10 absorbs light and causes the production of reactive oxygen species 50 (ROS). The reactive oxygen species is thus generated in close proximity to DNA 40, which it cleaves.

In addition, counterions will be associated with the complex. In one embodiment of the invention, the counterion is $PF_6^-$. However, other counterions exist that can also associate with the metal complex, including but not limited to $Cl^-$, $Br^-$, $I^-$, $CF_3SO_3^-$, $BF_4^-$, $NO_3^-$, $ClO_4^-$, $CO_3^{-2}$, $SO_4^{2-}$, etc. Those of skill in the art will recognize that many such suitable counterions exist and may be utilized to form the salt form of a complex without altering the fundamental properties of the complex, other than its solubility. Any suitable non-active counterion may be utilized.

This system differs from that of U.S. Pat. No. 6,962,910 to Brewer and Swavey (Nov. 8, 2005) the entire contents of which is hereby incorporated by reference, because there is no electron acceptor unit in these new complexes whereas it is a requirement for the systems described in U.S. Pat. No. 6,962,910. In addition, the present system requires molecular oxygen in order to function, which is not the case for the U.S. Pat. No. 6,962,910 system. In the present system, a reactive oxygen species cleaves the DNA through an MLCT system. In contrast, according to U.S. Pat. No. 6,962,910, DNA cleavage occurs as the result of an oxygen independent pathway through an MMCT excited state. In addition, an advantage of the present systems over those described in U.S. Pat. No. 6,962,910 is that the inclusion of the Pt DNA binding moiety allows targeting of the complex to DNA, resulting in more efficient delivery of the complexes to the site of action.

Figure 3:
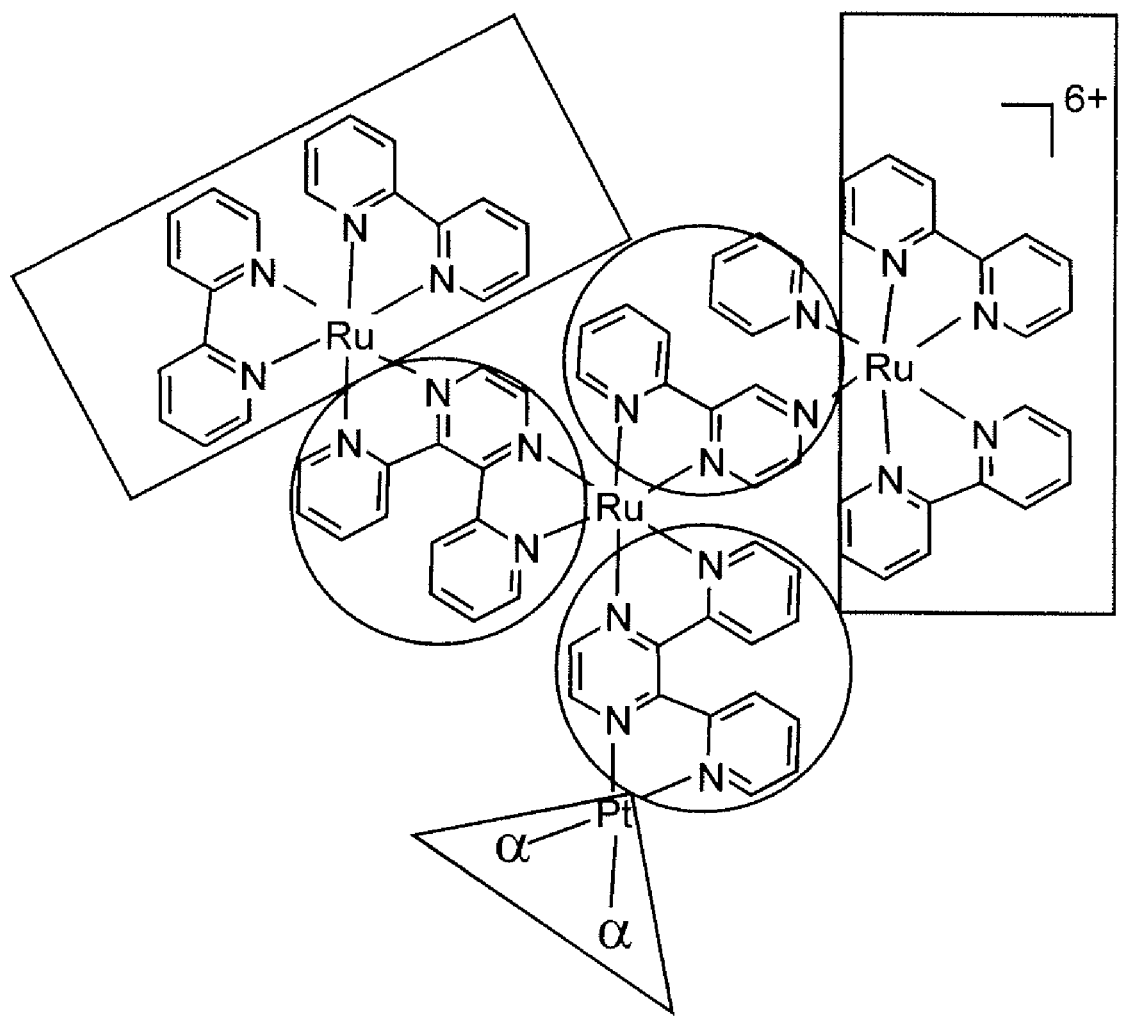
FIG. 3. The tetrametallic supramolecular complex [{(bpy)$_2$Ru(dpp)}$_2$Ru(dpp)PtCl$_2$]$^{6+}$ (bpy=2,2'-bipyridine, dpp=2,3-bis(2-pyridyl)pyrazine).

One exemplary supramolecular complex is [{(bpy)$_2$Ru (dpp)}$_2$Ru(dpp)PtCl$_2$](PF$_6$)$_6$ (bpy 2,2'-bipyridine, dpp=2,3-bis(2-pyridyl)pyrazine), which is depicted in FIG. 3. In FIG. 3, the Pt-based DNA binding component is shown within the triangle, the bridging moieties are shown in circles, and the MLCT moieties are shown in a rectangle, analogous to the depiction of these generic elements in FIGS. 1 and 2. Electronic absorption spectroscopy of this exemplary complex shows ligand based π→π* transitions in the UV with Ru based metal-to-ligand charge transfer (MLCT) transitions throughout much of the visible. The Ru-dpp CT centers at 542 nm (e=34500 $M^{-1}$ $cm^{-1}$). This exemplary complex has a highest occupied molecular orbital (HOMO) localized on peripheral Ru with $E_{1/2}^{oxd}$ at 1.58 V vs. Ag/AgCl, and a lowest unoccupied molecular orbital (LUMO) at the μ-dpp connecting Ru and Pt, $E_{1/2}^{red}$ at −0.40 V vs. Ag/AgCl. Synthesis of this complex and the investigation of its ability to bind and cleave DNA in the presence of light and molecular oxygen is described in Examples 1 and 2 below. Additional exemplary supramolecular complexes are illustrated in FIG. 4 and in Examples 3 and 4.

The supramolecular complexes of the invention thus comprise three coupled components. The function of the metal to ligand charge transfer light absorber is to produce an initially optically populated metal to ligand charge transfer state. Requirements of the bridging ligand are that it must coordinate to both the light absorbing metal and the Pt-based DNA binding unit. The requirement for the Pt-based DNA binding unit is that it must have the capability to bind to DNA while incorporated in the complex.

The exact number and type of MLCT light absorbers used in the supramolecular metallic complexes of the present invention may vary, depending on several factors including but not limited to: the desired excitation wavelength to be employed; the oxidation potential of interest for the metal based highest occupied molecular orbital; the required extinction coefficient for the excitation wavelength; ease of synthesis of the complex; cost and/or availability of components; and the like. Any suitable number of MLCT light absorbers may be used so long as within the complex an initial optically populated MLCT state is produced upon exposure to light or radiant energy, and which can produce a reactive oxygen species. In preferred embodiments, the number of MLCT light absorbers will range from 1 to about 14, and preferably from 1 to about 5, and more preferably from 1 to about 3.

Those of skill in the art will recognize that many suitable metals exist that can function as MLCT light absorbers in the practice of the present invention. Examples include but are not limited to ruthenium(II), osmium(II), rhenium(I), iron (II), platinum(II), etc. In preferred embodiments, three ruthenium(II) or three osmium(II) centers are utilized.

Those of skill in the art will recognize that a variety of Pt-based DNA binding agents are available and can be used successfully in the practice of the present invention. See, for example, Cisplatin and related anticancer drugs: Recent advances and insights. Barnes, Katie R.; Lippard, Stephen J. Department of Chemistry, Massachusetts Institute of Technology, Cambridge, Mass., USA. Metal Ions in Biological Systems (2004), 42 (Metal Complexes in Tumor Diagnosis and as Anticancer Agents), 143-177. Publisher: Marcel Dekker, Inc., CODEN:MIBSCD ISSN: 0161-5149. Journal; General Review written in English. CAN 142:272975 AN 2004: 615379 CAPLUS. Examples include but are not limited to Pt metals with one or more labile ligands, for example, cis-platin ($cisPtCl_2$).

The complexes of the present invention require the presence of at least one bridging ligand. By "bridging ligand" we mean that, in the supramolecular complex, the ligand is located or positioned (i.e. bonded, coordinated) between an MLCT light absorber and a Pt-based DNA binding unit. Further, if there is more than one MLCT light absorber in the complex, the bridging ligands will be positioned to attach each light absorbing unit to either another light absorbing unit or directly to the Pt-based DNA binding unit.

The bridging ligands coordinate or bind to the metal centers via donor atoms. Those of skill in the art will recognize that many suitable substances exist which contain appropriate donor atoms and may thus function as bridging ligands in the complexes of the present invention. These ligands fall into two categories, bridging and terminal ligands. Bridging ligands serve to connect metal centers and thus bind to or coordinate two separate metal centers. Terminal ligands bind or coordinate to only one metal center and serve to satisfy the needed coordination sphere for such metals and provide a means to tune both light absorbing and redox properties of that metal center. Examples of such ligands include, but are not limited to, substances with: nitrogen donor atoms (e.g. pyridine- and pyridimidine-containing moieties such as 2,2'-bipyridine ("bpy"); 2,2':6',2"-terpyridine ("tpy"); 2,3-bis(2-pyridyl)pyrazine ("dpp"); and 2,2'-bipyridimidine ("bpm"); 2,3-bis(2-pyridyl)quinoxaline; 2,3,5,6,-tetrakis(2-pyridyl)pyrazine; carbon and nitrogen donor atoms (e.g. 2,2'-phenylpyridine); phosphorus donor atoms (e.g. triphenylphosphine, diethylphenylphosphine); etc. In preferred embodiments of the present invention, the ligands are π-acceptors bpy, tpy, dpp and bpm.

Further, those of skill in the art will recognize that, depending on the number of available coordination sites on the metals to which the bridging ligands are coordinated, other extraneous ligands may also be present to complete the coordination sphere of the metal. Examples of such ligands include but are not limited to halogens such as Cl and Br, COOH, CO, $H_2O$, $CH_3CN$, etc.

The DNA cleaving agents of the present invention may be used for cleavage of DNA in many settings, including but not limited to cleavage of purified or partially purified DNA in laboratory setting for investigational purposes; and for the cleavage of DNA within cells, either ex vivo or in vivo. For example, ex vivo uses include cleavage of DNA in cultured cells for any reason, or of cells that have been removed from an individual with the intent of reintroducing the cells into the individual (or another individual) after manipulation of the cells (e.g. purging of tumor cells, genetic engineering of the cells, etc.) and the like.

Examples of in vivo uses include the cleavage of DNA of cells within an organism, especially unwanted hyperproliferating cells. The cleavage of the DNA of such cells damages and/or kills the cells. Those of skill in the art are familiar with cell types that are described as "hyperproliferating" or "hyperproliferative" or "over-proliferating". Those of skill in the art will recognize that these terms refer to cells that are growing, dividing, or proliferating at an inappropriate or non-normal time and/or place, and include cells that have entered the cell cycle when the should be in $G_0$ or in a quiescent state. Such cells include tumor or cancer cells (including but not limited to leukemia cells, ovarian cancer cells, Burkitt's lymphoma cells, breast cancer cells, gastric cancer cells, testicular cancer cells, prostate cancer cells, esophageal and lung cancer cells, skin cancer cells, and the like), and cells associated with psoriasis, warts, macular degeneration and other non-malignant hyperproliferating conditions. Discussions of hyperproliferating cells (both malignant and non-malignant) may be found, for example, in the following United States patents: U.S. Pat. No. 5,561,160 to Walasek et al. (Oct. 1, 1996); U.S. Pat. No. 5,670,151 to Larrick et al. (Sep. 23, 1997); U.S. Pat. No. 5,744,460 to Muller et al. (Apr. 28, 1998); U.S. Pat. No. 5,747,482 to Bernstein (May 5, 1998); U.S. Pat. No. 6,649,411 to Gozes et al. (Nov. 18, 2003); U.S. Pat. No. 6,673,894 to Zahner (Jan. 6, 2004); and U.S. Pat. No. 6,759,425 to Sircar et al. (Jul. 6, 2004), the complete contents of each of which are hereby incorporated by reference.

While one method of the present invention is principally intended to thwart replication of hyperproliferating cells, other cellular populations may be targeted as well. For example, cells infected by a pathological agent such as a virus or bacterium, may also be targeted. This application of the complexes would involve the steps of exposing the infected cells to the supramolecular complex followed by the exposure of the infected cells to activating light in the presence of oxygen from the air. The supramolecular complexes could thereby bind to the DNA of the virus or bacterium through the Pt DNA binding site and upon exposure to visible light generate a reactive oxygen species that will cleave the DNA leading to virus or bacterium cell death or inhibition of replication Those of skill in the art will recognize that many types of suitable formulations exist for administering the supramolecular agents, and many suitable methods for administration are also available. See, for example, U.S. Pat. No. 6,962,910 to Brewer et al. is one source of information about such formulations. Generally, the composition comprises at least one of the DNA cleaving agents and a suitable carrier, e.g. a suitable physiological carrier for in vivo administration, e.g. saline. The composition may be administered in any of a variety of suitable forms, including forms that include additional components such as buffers, stabilizers, nutrients, antioxidants, flavorings, colorants, and the like, which are appropriate to a means of administration. Those of skill in the art will recognize that the exact form will vary from application to application. The compounds can be administered in the pure form or in a pharmaceutically acceptable formulation including suitable elixirs, binders, and the like or as pharmaceutically acceptable salts or other derivatives. It should be understood that the pharmaceutically acceptable formulations and salts include liquid and solid materials conventionally utilized to prepare injectable dosage forms and solid dosage forms such as tablets and capsules. Water may be used for the preparation of injectable compositions which may also include conventional buffers and agents to render the injectable composition isotonic. Solid diluents and excipients include lactose, starch, conventional disintegrating agents, coatings and the like. Preservatives such as methyl paraben or benzalkium chloride may also be used. Depending on the formulation, it is expected that the active composition will consist of 1-99% of the composition and the vehicular "carrier" will constitute 1-99% of the composition.

Likewise, the dosage, frequency and timing of administration will vary from case to case and will depend on factors such as the particular application, the nature and stage of a condition resulting from hyperproliferation of cells (e.g. size and location of a malignant or non-malignant tumor), characteristics of the patient (e.g. overall health, age, weight, gender and the like), and other factors such as ancillary treatments (chemotherapy, radiotherapy, and the like). The details of administration are best determined by a skilled practitioner such as a physician. Further, the details of administration are normally worked out during clinical trials. However, the approximate dosage range will preferably be from about 0.1 to 10 mg of agent per kg of weight, and more preferably from about 0.25 to 1.0 mg/kg. When treating DNA directly, the amount of agent to be administered is preferably in the range of about 0.1-50 μg per about 0.1-50 μg of DNA, and more preferably, in the range of about 1-10 μg per about 1-10 μg of DNA. Those of skill in the art will recognize that the precise amounts will vary depending, for example, on the precise characteristics of the complex and the DNA itself, on temperature, pH, and the like. Typically, the agent will be administered about 1 to 24 hours prior to exposure to a suitable light source, and preferably from about 1 to 4 hours prior to exposure to the light source.

Likewise, the dose or frequency of illumination of the target cells will vary from case to case, but will generally be in the range of 25-200 $J/cm^2$ light dose, 25-200 $mW/cm^2$ fluence rate (see Ochsner, M. 1997. Photodynamic Therapy: the Clinical Perspective. Review on applications for control of diverse tumours and non-tumour diseases. *Drug Res.*, 47:1185-1194).

The compounds of the invention also require oxygen to cleave DNA. Those of skill in the art will recognize that intracellular oxygen levels are sufficient to support the use of the complexes for this purpose. This is also the case, for example, for known photodynamic therapy agents (e.g. porphyrins), which also require oxygen to function, and for which the presence of intracellular oxygen is sufficient.

EXAMPLES

Example 1

Ru polyazine complexes have been applied in diverse arenas due in part to their strong visible light absorbing ability, often emissive metal-to-ligand charge transfer (MLCT) excited states, and tunable properties.[1] The incorporation of polyazine bridging ligands has allowed for the construction of complex systems with diverse building blocks that take advantage of the rapid intramolecular energy and electron transfer processes in these assemblies. Supramolecular complexes incorporating Ru light absorbers (LAs) have been extensively studied for their potential applications in a variety of light activated processes.[2-6] Despite the large number of Ru polyazine supramolecular assemblies developed to date, few couple reactive metals such as Pt to these LA units despite the promise such systems hold.[7-12]

A number of metal complexes have the ability to target DNA and interact in a variety of ways, often allowing these compounds to function as anti-cancer agents.[13-25] Interactions with DNA have been shown to include both covalent binding and noncovalent interactions, such as intercalation between the DNA base pairs. Binding of a metal complex often leads to inhibition of transcription and/or replication of DNA. Some metal complexes can also be employed as photodynamic therapy (PDT) agents, inhibiting cell function via light mediated DNA cleavage.[13,14]

A well known class of DNA binding metal complexes is based on cisplatin, cis-[Pt(H$_3$)$_2$Cl$_2$].[15-17] The effectiveness of Pt in binding DNA led to the development of many cisplatin analogues.[10,18-20] Incorporation of LA metal units into this structural motif has been used to develop spectroscopic tags including complexes such as [(bpy)$_2$Ru(dpp)PtCl$_2$]$^{2+}$[10] and [(tpy)RuCl(dpp)PtCl$_2$]$^{+}$[7] (bpy=2,2'-bipyridine, tpy=2,2':6', 2"-terpyridine). The addition of LA units into this structural motif opens up the possibility of photoactivation.

Metal complexes capable of cleaving DNA using low energy visible light are also of particular importance as potential PDT agents. Metal complexes can photocleave DNA or more commonly sensitize molecular oxygen to cleave DNA.[21-23] Ruthenium based light absorbers with polyazine ligands have shown the ability to photocleave DNA directly or indirectly through oxygen mediated pathways.[13,14,21,24,25]

Reported herein is the coupling of a cis-dichloroplatinum (II) DNA binding site to a three metal Ru polyazine DNA photocleavage unit, [{(bpy)$_2$Ru(dpp)}$_2$Ru(dpp)PtCl$_2$] (PF$_6$)$_6$, (dpp=2,3-bis(2-pyridyl)pyrazine) (see FIG. 3). The new supramolecular complex has been synthesized, characterized, and tested for DNA binding and photocleavage properties. This supramolecular assembly represents the first such multifunctional DNA binding and photocleavage agent constructed from this polyazine structural motif. A building block synthetic method is used to synthesize the trimetallic Ru chromophore [{(bpy)$_2$Ru(dpp)}$_2$Ru(dpp)](PF$_6$)$_6$[26] prior to the final step of adding cis-PtCl$_2$. Detailed synthetic information can be found in supporting information.[3,27,28]

The [{(bpy)$_2$Ru(dpp)}$_2$Ru(dpp)PtCl$_2$](PF$_6$)$_6$ supramolecular assembly was characterized by FAB and MALDI-TOF MS, electronic absorption spectroscopy and electrochemistry.[3,29-31] The FAB-MS and MALDI-TOF MS are consistent with the supramolecular complex structure, and are included in supporting information. The light absorbing and redox properties of this supramolecular complex are indicative of their composition, displaying properties consistent with each structural sub-unit.

The electrochemical properties of supramolecular complexes of this type are indicative of the number and type of sub-units with oxidations being metal based and reductions typically being ligand based.[3] When the ligand dpp is bridging between two electropositive metals like Ru(II) and Pt(II), the p* acceptor orbitals are stabilized and the dpp possesses two sequential one electron reductions prior to terminal bpy reductions. The electrochemical properties of [{(bpy)$_2$Ru(dpp)}$_2$Ru(dpp)PtCl$_2$](PF$_6$)$_6$ are summarized in tabular form in Table 1. The oxidation couple at 1.58 V corresponds to the two peripheral RuII/III processes in [{(bpy)$_2$Ru(dpp)}$_2$Ru(dpp)PtCl$_2$](PF$_6$)$_6$, consistent with their coordination. By comparing the newly-prepared [{(bpy)$_2$Ru(dpp)}$_2$Ru(dpp)PtCl$_2$](PF$_6$)$_6$ and the trimetallic system [{(bpy)$_2$Ru(dpp)}$_2$Ru(dpp)](PF$_6$)$_6$, we observe a shift in the reduction potential for the formally terminal dpp from −1.08 V to −0.40 V vs. Ag/AgCl. The other two μ-dpp's connecting peripheral Ru to the central Ru reduce at −0.60 and −0.71 V, respectively.

TABLE 1

Electrochemical properties for [{(bpy)$_2$Ru(dpp)}$_2$Ru(dpp)PtCl$_2$](PF$_6$)$_6$ in 0.1M Bu$_4$NPF$_6$/acetonitrile vs. Ag/AgCl where bpy = 2,2'bipyridine and dpp = 2,3-bis(2-pyridyl)pyrazine.

| Complex | $E_{1/2}$ (V) | |
|---|---|---|
| | Oxidations | Reductions |
| [{(bpy)$_2$Ru(dpp)}$_2$Ru(dpp)](PF$_6$)$_6$ | 1.58 Ru$^{III/II}$ | −0.50 dpp$^{0/-}$ |
| | | −0.64 dpp$^{0/-}$ |
| | | −1.08 dpp$^{0/-}$ |
| | | −1.21 dpp$^{-/2-}$ |
| | | −1.36 dpp$^{-/2-}$ |
| | | −1.52 dpp$^{-/2-}$ |
| [{(bpy)$_2$Ru(dpp)}$_2$Ru(dpp)PtCl$_2$](PF$_6$)$_6$ | 1.58 Ru$^{III/II}$ | −0.40 dpp$^{0/-}$ |
| | | −0.60 dpp$^{0/-}$ |
| | | −0.71 dpp$^{0/-}$ |
| | | −1.12 dpp$^{-/2-}$ |
| | | −1.22 dpp$^{-/2-}$ |
| | | −1.30 dpp$^{-/2-}$ |

Figure 5:
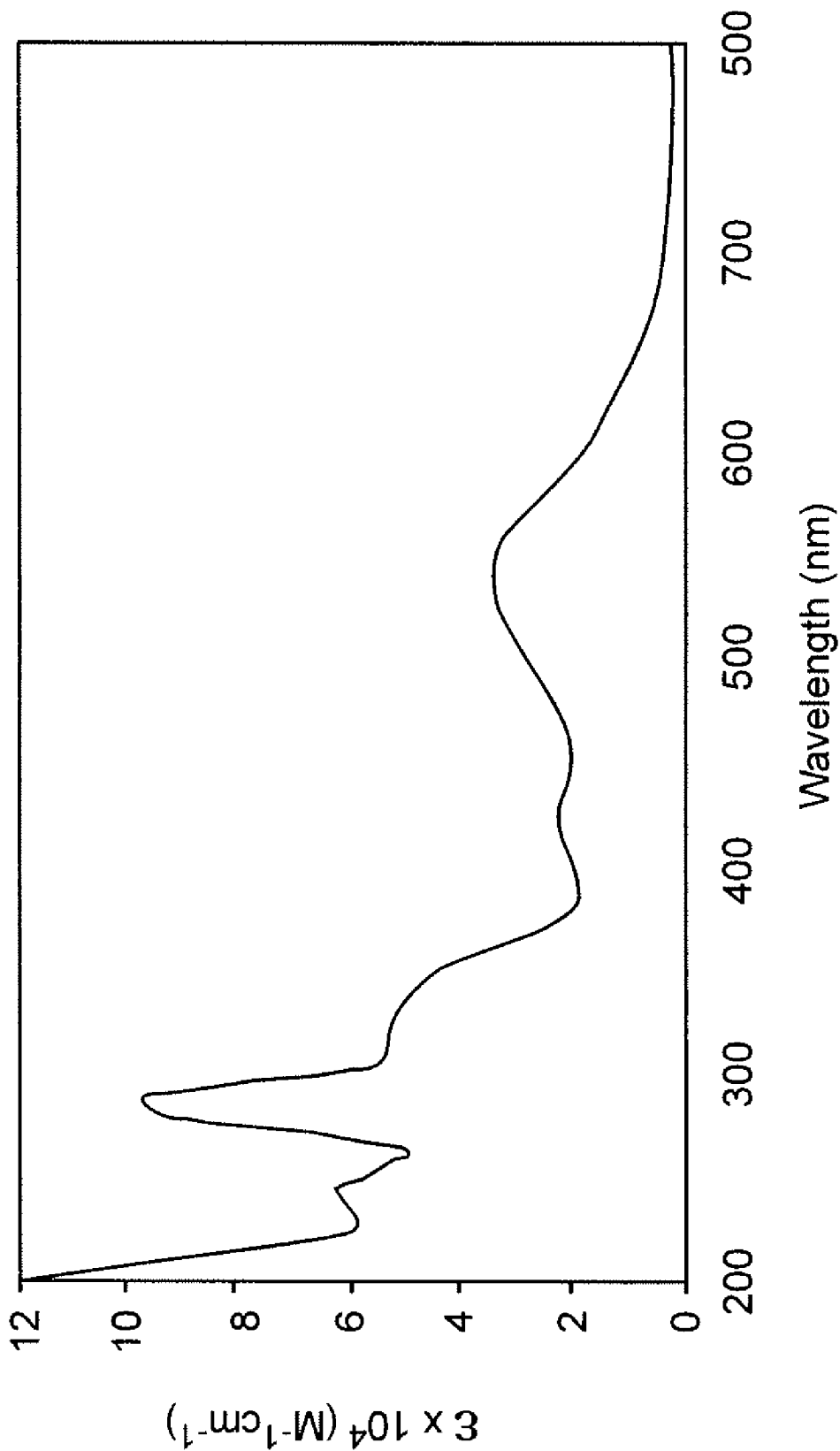
FIG. 5. Electronic absorption spectrum of [{(bpy)$_2$Ru(dpp)}$_2$Ru(dpp)PtCl$_2$](PF$_6$)$_6$ in CH$_3$CN at room temperature (bpy=2,2'-bipyridine, dpp=2,3-bis(2-pyridyl)pyrazine).

Electronic absorption spectroscopy is used to study the light absorbing properties of Ru polyazine supramolecular complexes.[3] These complexes usually show intense peaks in the UV region corresponding to ligand-based π→π* transition with overlapping MLCT transitions in visible region. FIG. 5 shows the electronic absorption spectrum for [{(bpy)$_2$Ru(dpp)}$_2$Ru(dpp)PtCl$_2$](PF$_6$)$_6$ in acetonitrile. The UV contains π→π* transitions for bpy and dpp with the peak at 290 nm corresponds to the bpy π→π* transitions and the shoulder 320 nm characteristic of μ-dpp π→π* transitions. The Ru(dπ)→bpy(π*) CT transition occurs at 416 nm and peaks at ca. 520-540 nm correspond to the Ru(dπ)→μ-dpp(π*) and Ru(dπ)→μ-dpp(π*) CT transitions. The extinction coefficient for peak at 542 nm is 34500 M$^{-1}$ cm$^{-1}$, consistent with the number of overlapping MLCT's in this region. The exemplary tetrametallic [{(bpy)$_2$Ru(dpp)}$_2$Ru(dpp)PtCl$_2$](PF$_6$)$_6$ is an efficient light absorber throughout the UV and visible regions.

Figure 6:
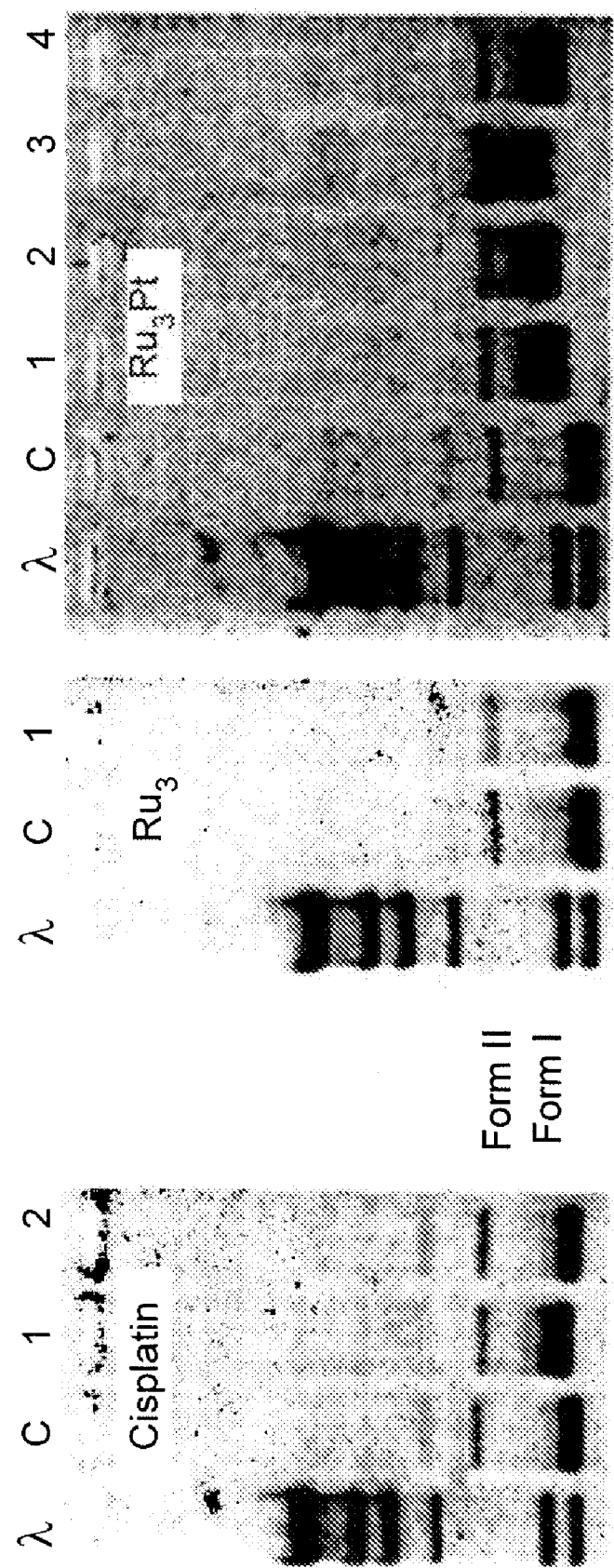
FIG. 6. DNA binding and photocleavage by [{(bpy)$_2$Ru(dpp)}$_2$Ru(dpp)PtCl$_2$](PF$_6$)$_6$ (Ru$_3$Pt) assayed with 0.8% agarose gel electrophoresis post stained with ethidium bromide using circular plasmid pUC18 DNA with comparison to cis-[Pt(NH$_3$)$_2$Cl$_2$] (Cisplatin) and [{(bpy)$_2$Ru(dpp)}$_2$Ru(dpp)](PF$_6$)$_6$ (Ru$_3$) (bpy=2,2'-bipyridine, dpp=2,3-bis(2-pyridyl) pyrazine). Lanes λ are the molecular weight standards (23, 9.4, 6.6, 4.4, 2.3, and 2.0 kb), lanes C are the DNA controls showing mostly form I and minor form II pUC18 DNA. The cisplatin lane 1 is a 5:1 base pair (BP):metal complex (MC) and lane 2 a 20:1 BP:MC incubated for 1 hour at 37° C. The Ru$_3$ lane 1 is a 20:1 BP:MC incubated for 1 hour at 37° C. The Ru$_3$Pt lane 1 is 20:1 BP:MC kept in the dark at room temperature, lane 2 is 20:1 BP:MC incubated for 1 hour in the dark at 37° C., lane 3 is 20:1 BP:MC photolyzed with 450 nm-1000 nm light for 1 hour under atmospheric conditions, lane 4 is 20:1 BP:MC photolyzed with 450 nm-1000 nm light for 1 hour under argon.

The DNA binding and photocleavage ability of the exemplary complex, [{(bpy)$_2$Ru(dpp)}$_2$Ru(dpp)PtCl$_2$](PF$_6$)$_6$, has been investigated using gel electrophoresis. The cis-dichloroplatinum(II) moiety is designed to allow the complex to bind covalently to DNA. The Ru polyazine units are designed to allow the complex to undergo sensitization of molecular oxygen leading to DNA photocleavage. The presence of the cis-dichloroplatinum(II) sub-unit delivers the Ru polyazine sub-unit to its target prior to optical excitation. DNA interactions of [{(bpy)$_2$Ru(dpp)}$_2$Ru(dpp)PtCl$_2$](PF$_6$)$_6$ were compared to a binding analyses of Ru$_3$ and cisplatin using gel electrophoresis and pUC18 circular plasmid DNA, (2686 BP, Bayou Biolabs) post-stained with ethidium bromide. The results are presented in FIG. 6. Lanes λ are the molecular weight standards (23, 9.4, 6.6, 4.4, 2.3, and 2.0 kb). Lanes C are the pUC18 DNA controls, showing primarily the supercoiled (form I) and minor nicked (form II) forms of the circular pUC18 plasmid. The lane 1 for cisplatin is a 5:1 base pairs (BP):metal complex (MC) and lane 2 is a 20:1 BP:MC solution incubated at 37° C. for 1 hr. The migration of form I of the pUC18 is retarded by the known coordination of cisplatin to the DNA while form II migration is slightly enhanced upon DNA binding. The lane 1 of Ru$_3$ is a 20:1 BP:MC solution incubated at 37° C. for 1 hr showing that migration of the DNA is not impacted by addition of the Ru$_3$ complex, consistent with this complex's expected lack of coordination to DNA. Lane 1 of "Ru3Pt" is the 20:1 DNA BP:MC solution of [{(bpy)$_2$Ru(dpp)}$_2$Ru(dpp)PtCl$_2$](PF$_6$)$_6$ incubated at 37° C. for 1 hr. This lane shows a decreased migration of the form I pUC18 through the gel, indicative of the coordination of Ru$_3$Pt to the DNA through the Pt site. The form II of pUC18 also shows slightly slowed migration consistent with coordination by this large, highly cationic supramolecular assembly increasing the size and decreasing the negative charge of the plasmid. Lane 2 shows the same 20:1 BP:MC mixture incubated at 37° C. for 1 hour, displaying a similar retardation of migration through the gel, showing no enhancement of covalent binding by incubation. Lane 3 shows the same 20:1 BP:MC solution photolyzed $\lambda_{irr}$>450 nm for 1 hour, under atmospheric conditions. There is an appreciable conversion of the supercoiled (form 1) to nicked (form II) DNA, indicative of DNA photocleavage. Lane 4 is a 20:1 BP:MC solution photolyzed at λ>450 nm for 1 hour, under argon. In the absence of molecular oxygen, no DNA photocleavage is observed, consistent with the molecular design.

The multifunctional supramolecular complex [{(bpy)$_2$Ru(dpp)}$_2$Ru(dpp)PtCl$_2$] (PF$_6$)$_6$ has been prepared and shown to display both Pt based DNA binding and Ru based DNA photocleavage. Mass spectroscopy, electrochemistry and electronic absorption spectroscopy are consistent with the composition of this tetrametallic assembly. This complex has the ability to interact with DNA through two distinct pathways using each of the two built-in bioactive sub-units. The complex can both bind DNA through the cis-dichloroplatinum(II) unit and photochemically sensitize molecular oxygen to cleave DNA through the Ru polyazine unit. The ability to deliver and anchor the drug directly to the target can be useful in anti-cancer drug development. The covalent binding through Pt directs the cleavage to the DNA binding sites and enhances efficiency by a pre-localization at the target.

REFERENCES FOR EXAMPLE 1

1. Juris, A.; Balzani, V.; Barigelletti, F.; Campagna, S.; Belser, P.; Vonzelewsky, A. Coord. Chem. Rev. 1988, 84, 85.
2. Balzani, V.; Gomez-Lopez, M.; Stoddart, J. F. Acc. Chem. Res. 1998, 31, 405.
3. Balzani, V.; Juris, A.; Venturi, M.; Campagna, S.; Serroni, S. Chem. Rev. 1996, 96, 759.
4. Beer, P. D.; Hayes, E. J. Coord. Chem. Rev. 2003, 240, 167.
5. Bignozzi, C. A.; Argazzi, R.; Kleverlaan, C. J. Chem. Soc. Rev. 2000, 29, 87.
6. Gratzel, M. Coord. Chem. Rev. 1991, 111, 167.
7. Williams, R. L.; Toft, H. N.; Winkel, B.; Brewer, K. J. Inorg. Chem. 2003, 42, 4394.
8. Molnar, S. M.; Nallas, G.; Bridgewater, J. S.; Brewer, K. J. J. Am. Chem. Soc. 1994, 116, 5206.
9. Swavey, S.; Brewer, K. J. Inorg. Chem. 2002, 41, 6196.
10. Yam, V. W. W.; Lee, V. W. M.; Cheung, K. K. Organometallics 1997, 16, 2833.
11. Sommovigo, M.; Denti, G.; Serroni, S.; Campagna, S.; Mingazzini, C.; Mariotti, C.; Juris, A. Inorg. Chem. 2001, 40, 3318.
12. Serroni, S.; Juris, A.; Campagna, S.; Venturi, M.; Denti, G.; Balzani, V. J. Am. Chem. Soc. 1994, 116, 9086.
13. Boerner, L. J. K.; Zaleski, J. M. Curr. Opin. Chem. Biol. 2005, 9, 135.
14. Sharman, W. M.; Allen, C. M.; van Lier, J. E. Drug Discov. Today 1999, 4, 507.
15. Howegrant, M.; Wu, K. C.; Bauer, W. R.; Lippard, S. J. Biochemistry 1976, 15, 4339.
16. Lippard, S. J.; Bond, P. J.; Wu, K. C.; Bauer, W. R. Science 1976, 194, 726.
17. Jamieson, E. R.; Lippard, S. J. Chem. Rev. 1999, 99, 2467.
18. Milkevitch, M.; Storrie, H.; Brauns, E.; Brewer, K. J.; Shirley, B. W. Inorg. Chem. 1997, 36, 4534.
19. Milkevitch, M.; Brauns, E.; Brewer, K. J. Inorg. Chem. 1996, 35, 1737.
20. Yam, V. W. W.; Tang, R. P. L.; Wong, K. M. C.; Cheung, K. K. Organometallics 2001, 20, 4476.
21. Hergueta-Bravo, A.; Jimenez-Hernandez, M. E.; Montero, F.; Oliveros, E.; Orellana, G. J. Phys. Chem. B 2002, 106, 4010.
22. Kurbanyan, K.; Nguyen, K. L.; To, P.; Rivas, E. V.; Lueras, A. M. K.; Kosinski, C.; Steryo, M.; Gonzalez, A.; Mah, D. A.; Stemp, E. D. A. Biochemistry 2003, 42, 10269.
23. Yavin, E.; Stemp, E. D. A.; Weiner, L.; Sagi, I.; Arad-Yellin, R.; Shanzer, A. J. Inorg. Biochem. 2004, 98, 1750.
24. Fleisher, M. B.; Waterman, K. C.; Turro, N. J.; Barton, J. K. Inorg. Chem. 1986, 25, 3349.
25. Abdel-Shafi, A. A.; Worrall, D. R.; Ershov, A. Y. Dalton Trans. 2004, 30.
26. Puntoriero, F.; Serroni, S.; Galletta, M.; Juris, A.; Licciardello, A.; Chiorboli, C.; Campagna, S.; Scandola, F. Chemphyschem. 2005, 6, 129.
27. Brauns, E.; Jones, S. W.; Clark, J. A.; Molnar, S. M.; Kawanishi, Y.; Brewer, K. J. Inorg. Chem. 1997, 36, 2861.
28. Richter, M. M.; Brewer, K. J. Inorg. Chem. 1993, 32, 5762.
29. Asara, J. M.; Uzelmeier, C. E.; Dunbar, K. R.; Allison, J. Inorg. Chem. 1998, 37, 1833.
30. Lou, X.; van Buijtenen, J.; Bastiaansen, J. J. A. M.; de Waal, B. F. M.; Langeveld, B. M. W.; van Dongen, J. L. J. J. Mass Spectrom. 2005, 40, 654.
31. Marcaccio, M.; Paolucci, F.; Paradisi, C.; Carano, M.; Roffia, S.; Fontanesi, C.; Yellowlees, L. J.; Serroni, S.; Campagna, S.; Balzani, V. J. Electroanal. Chem. 2002, 532, 99.

Example 2

Preparation and Analysis of an Exemplary Supramolecular Complex Materials

The metals RuCl$_3$.xH$_2$O and K$_2$PtCl$_4$ are from Alfar Aesar and bpy (2,2'-bipyridine), dpp (2,3-bis(2-pyridyl)pyrazine)

and AgCF$_3$SO$_3$ from Aldrich and are used without further purification. All the solvents are HPLC grade and used without further purification. [{(bpy)$_2$Ru(dpp)}$_2$RuCl$_2$](PF$_6$)$_6$ is prepared according to literature method.[3]

[{(bpy)$_2$Ru(dpp)}$_2$Ru(dpp)PtCl$_2$](PF$_6$)$_6$. A standard building block method is used.[5] A 1.2 g (0.59 mmol) sample of [{(bpy)$_2$Ru(dpp)}$_2$RuCl$_2$](PF$_6$)$_6$ is reacted with excess AgCF$_3$SO$_3$ (0.82 g, 4.0 mmol) for 2 hrs to remove the chloride. The AgCl precipitate is removed by filtration and the filtrate is reacted with excess dpp in 95% ethanol for 24 hours to prepare the [{(bpy)$_2$Ru(dpp)}$_2$Ru(dpp)](PF$_6$)$_6$ (1.2 g, 81% yield). Pt(DMSO)$_2$Cl$_2$ is prepared from K$_2$PtCl$_4$ according to literature method.[6] In the final step e, 150 mg (0.060 mmol) [{(bpy)$_2$Ru(dpp)}$_2$Ru(dpp)](PF$_6$)$_6$ and 47 mg (0.10 mmol) Pt(DMSO)$_2$Cl$_2$ are mixed in 25 ml 95% ethanol and heated to reflux for 39 hours. Addition of saturated KPF$_6$ solution induces precipitation and the product is collected by vacuum filtration. Then the product is dissolved in a minimal amount of acetonitrile and flash precipitated in diethyl ether, collected by vacuum filtration and dried by rinsing with diethyl ether.

Figure 7:
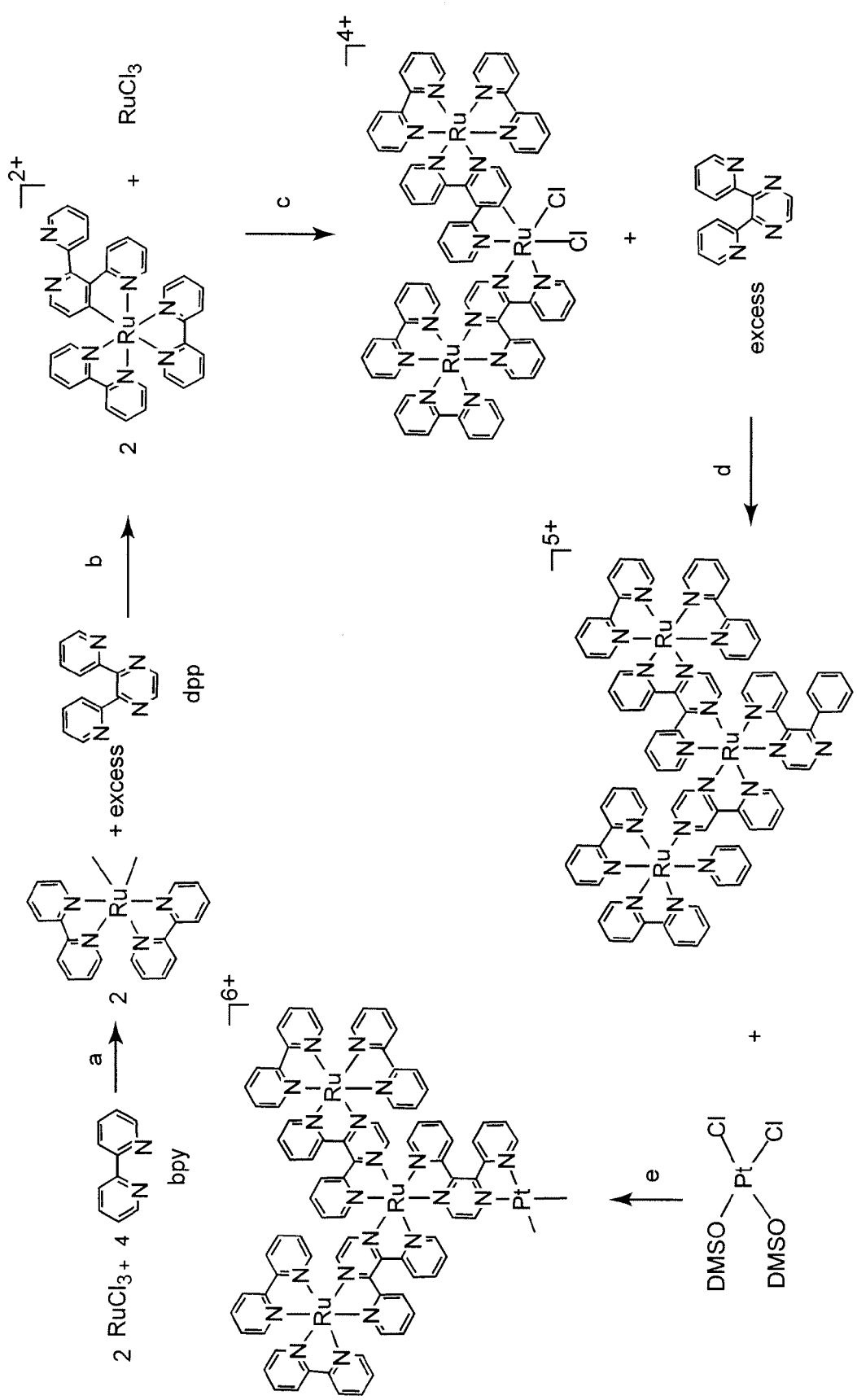
FIG. 7. Synthetic route to prepare the tetrametallic [{(bpy)$_2$Ru(dpp)}$_2$Ru(dpp)PtCl$_2$](PF$_6$)$_6$ where bpy=2,2'-bipyridine, dpp=2,3-bis(2-pyridyl)pyrazine.

This synthetic route is schematically illustrated in FIG. 7.

Electrochemistry. A Bioanalytical Systems, Inc. electrochemical workstation was used to generate cyclic voltammograms. In all cases, 0.1 M Bu$_4$NPF$_6$ in acetonitrile served as the solvent supporting electrolyte system. The three-electrode system consists of a platinum disk working electrode, a platinum wire auxiliary electrode, and a Ag/AgCl reference electrode (0.286 V vs. NHE). The reference electrode was calibrated against the ferrocene/ferrocenium couple reported as 0.665 V vs. NHE in a 0.1 M Bu4NPF6/acetonitrile solution.[7] The platinum working electrode was polished between scans, and the solutions were deoxygenated by bubbling with argon.

Electronic Absorption Spectroscopy. Spectra were generated at room temperature in a 1 cm quartz cuvette using a Hewlett-Packard 8452 diode array spectrometer with a 2 nm resolution and a spectral range of 190 to 820 nm.

Figure 8:
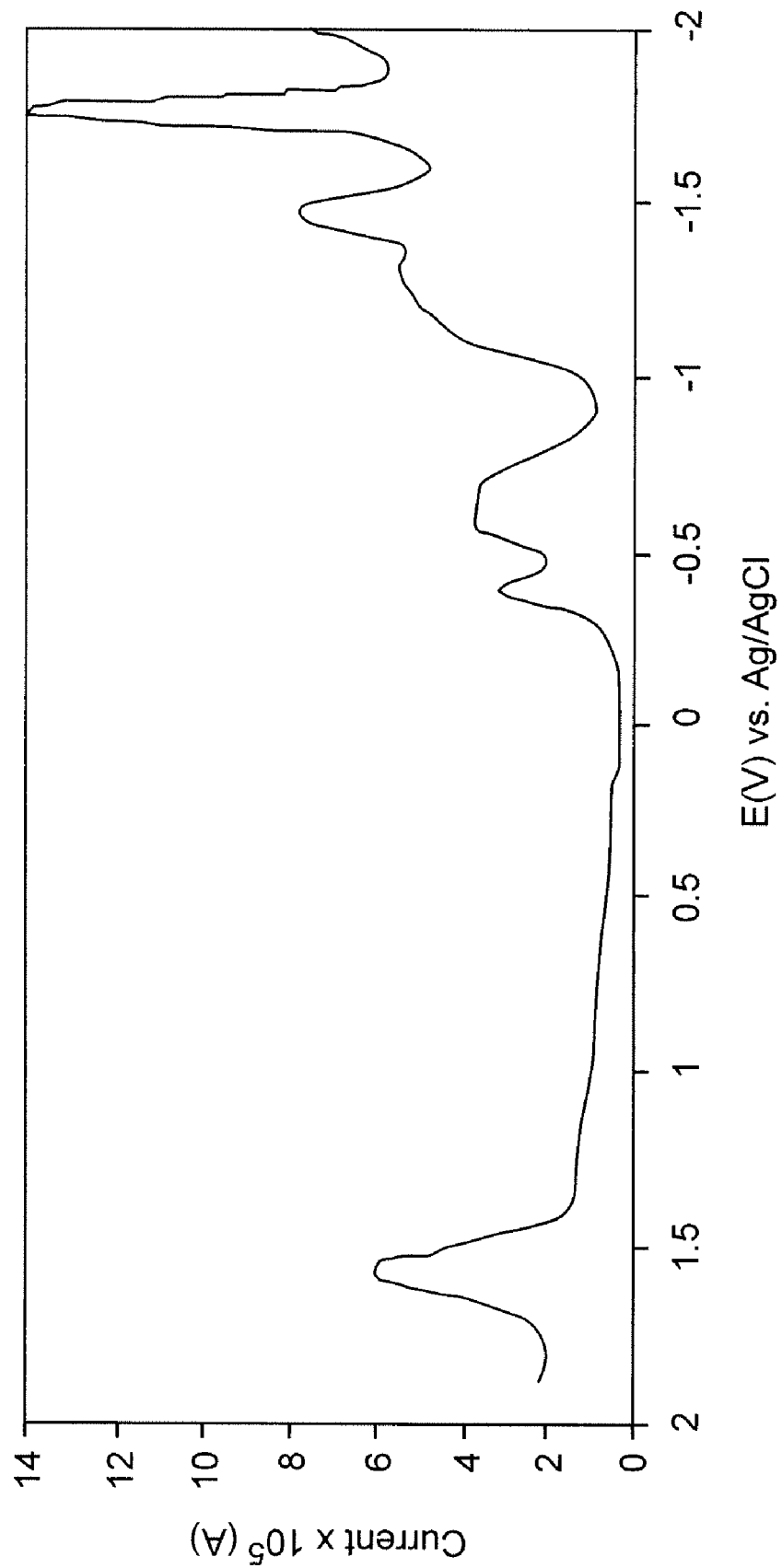
FIG. 8. Square wave voltammogram of [{(bpy)$_2$Ru(dpp)}$_2$Ru(dpp)PtCl$_2$](PF$_6$)$_6$ measured in 0.1 M Bu$_4$NPF$_6$ CH$_3$CN solution at room temperature at a scan rate 200 mV/s (bpy=2,2'-bipyridine, dpp=2,3-bis(2-pyridyl)pyrazine).

Mass Spectral Analysis. FAB and MALDI-TOF MS analysis were performed by M-Scan Inc. at West Chester, Pa. The FAB-MS is performed on a VG Analytical ZAB 2-SE high field mass spectrometer using m-nitrobenzyl alcohol as a matrix and the MALDI-TOF MS is performed on a Applied Biosystems Voyager-DE Pro using 2,5-dihydroxybenzoic acid as a matrix (excited at 337 nm). The compounds tested displayed peak patterns consistent with their formulation showing loss of intact ligands and PF6-counterions. The data is presented in FIG. 8, and in tabular form in Tables 2 and 3.

TABLE 2

FAB-MS data summary for the
[{(bpy)$_2$Ru(dpp)}$_2$Ru(dpp)PtCl$_2$](PF$_6$)$_6$
supramolecular complex (bpy = 2,2'-bipyridine,
dpp = 2,3-bis(2-pyridyl)pyrazine).

| MS Data | Peak (m/z) | Abundance | Fragment |
|---|---|---|---|
| FAB | 2623.1 | 36 | (M-PF$_6$ + H)$^+$ |
| | 2477.3 | 100 | (M-2PF$_6$ + H)$^+$ |
| | 2331.6 | 57 | (M-3PF$_6$)$^+$ |
| | 2183.9 | 18 | (M-4PF$_6$-3H)$^+$ |

TABLE 3

MALDI-MS data summary for the
[{(bpy)$_2$Ru(dpp)}2Ru(dpp)PtCl$_2$](PF$_6$)$_6$
supramolecular complex (bpy = 2,2'-bipyridine,
dpp = 2,3-bis(2-pyridyl)pyrazine).

| MS Data | Peak (m/z) | Abundance | Fragment |
|---|---|---|---|
| MALDI | 2482 | 21 | (M-2PF$_6$ + 6H)$^+$ |
| | 2339 | 81 | (M-3PF$_6$ + 7H)$^+$ |
| | 2196 | 100 | (M-4PF$_6$ + 9H)$^+$ |
| | 2049 | 45 | (M-5PF$_6$ + 7H)$^+$ |
| | 1362 | 72 | (M-4PF$_6$-2[(bpy)$_2$Ru] + 2H)$^+$ |
| | 1207 | 58 | (M-6PF$_6$-4bpy-2Cl + 6H)$^+$ |

REFERENCES FOR EXAMPLE 2

1. Sullivan, B. P.; Salmon, D. J.; Meyer, T. J. Inorg. Chem. 1978, 17, 3334.
2. Braunstein, C. H.; Baker, A. D.; Strekas, T. C.; Gafney, H. D. Inorg. Chem. 1984, 23, 857.
3. Richter, M. M.; Brewer, K. J. Inorg. Chem. 1993, 32, 5762.
4. Puntoriero, F.; Serroni, S.; Galletta, M.; Juris, A.; Licciardello, A.; Chiorboli, C.; Campagna, S.; Scandola, F. Chem Phys Chem 2005, 6, 129.
5. Balzani, V.; Campagna, S.; Denti, G.; Juris, A.; Serroni, S.; Venturi, M. Acc. Chem. Res. 1998, 31, 26.
6. Williams, R. L.; Toft, H. N.; Winkel, B.; Brewer, K. J. Inorg. Chem. 2003, 42, 4394.
7. Gennett, T.; Milner, D. F.; Weaver, M. J. J. Phys. Chem. 1985, 89, 2787.

Example 3

Mixed-Metal Complexes with Other Bridging Ligands

Figure 9:
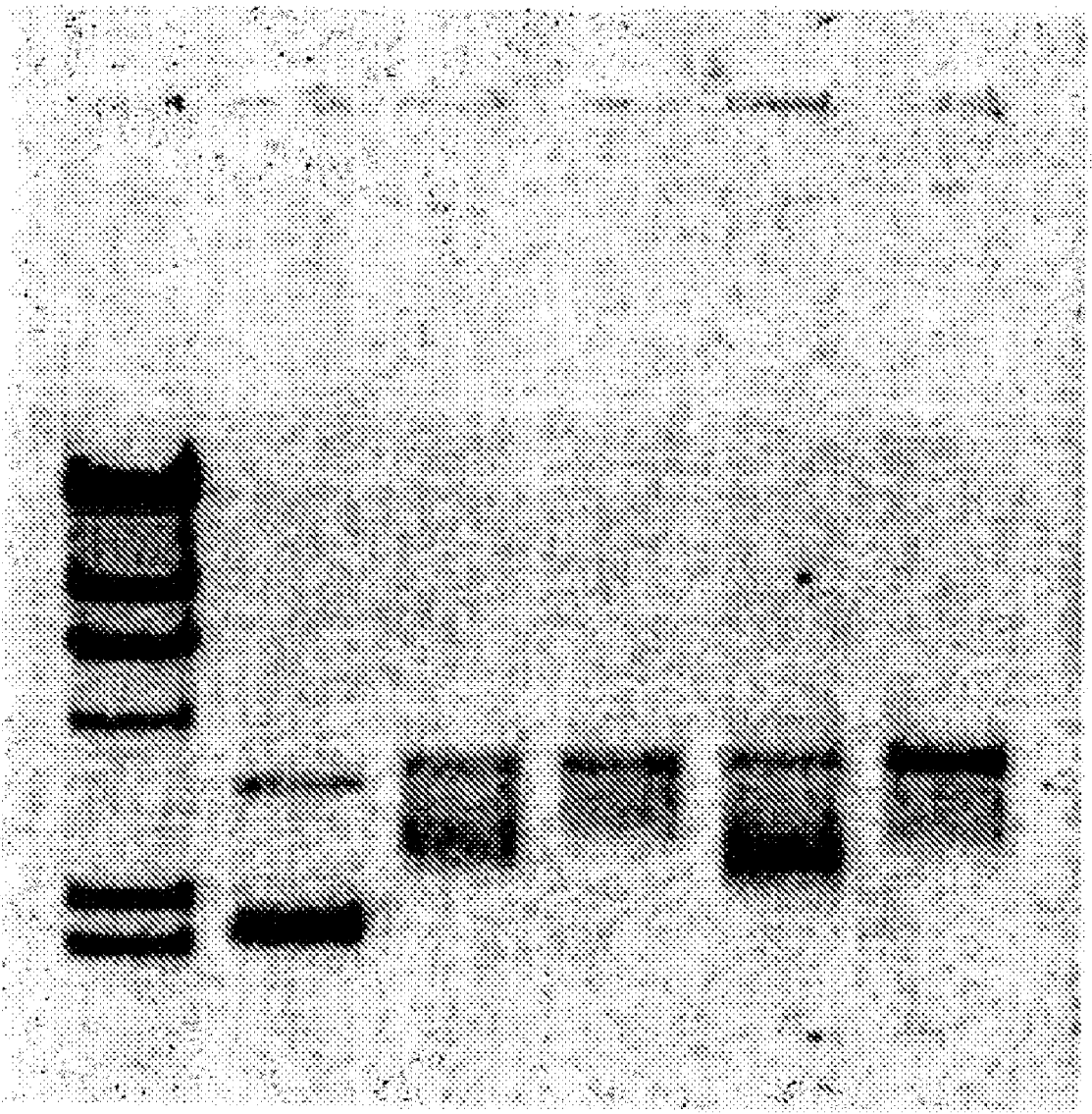
FIG. 9. DNA binding and photocleavage by [{(bpy)$_2$Ru(dpp)}$_2$Ru(dpq)PtCl$_2$](PF$_6$)$_6$. Lane 1 is the molecular weight standard, lane C is the pUC18 DNA plasmid control, lane 25° is 10:1 metal complex:DNA base pair incubated at 25° C., lane 37° is the 10:1 ratio incubated at 37° C., Ar* is the 10:1 ratio photolyzed for 1 hour under Ar, lane O$_2$* is the 10:1 ratio photolyzed under ambient atmosphere.

A mixed-metal complex, [{(bpy)$_2$Ru(dpp)}$_2$Ru(dpq)PtCl$_2$](PF$_6$)$_6$, was synthesized using bridging ligands dpq (2,3-bis(2-pyridyl)quinoxaline), and dpp (the ligand described in Example 1). The complex was tested for its ability to bind DNA and to photocleave the DNA in an O$_2$ dependent manner by incubating the complex with DNA in the ambient atmosphere and under argon. The results are presented in FIG. 9. As can be seen, the complex was effective in binding to DNA under with and without O$_2$. However, the DNA was cleaved only when O$_2$ was present, and not in the absence of O$_2$. This illustrates the metal complex binds to DNA and photocleaves DNA in a oxygen dependent manner.

Example 4

Mixed-Metal Complexes with Other Bridging Ligands and Other Metals

Figure 10:
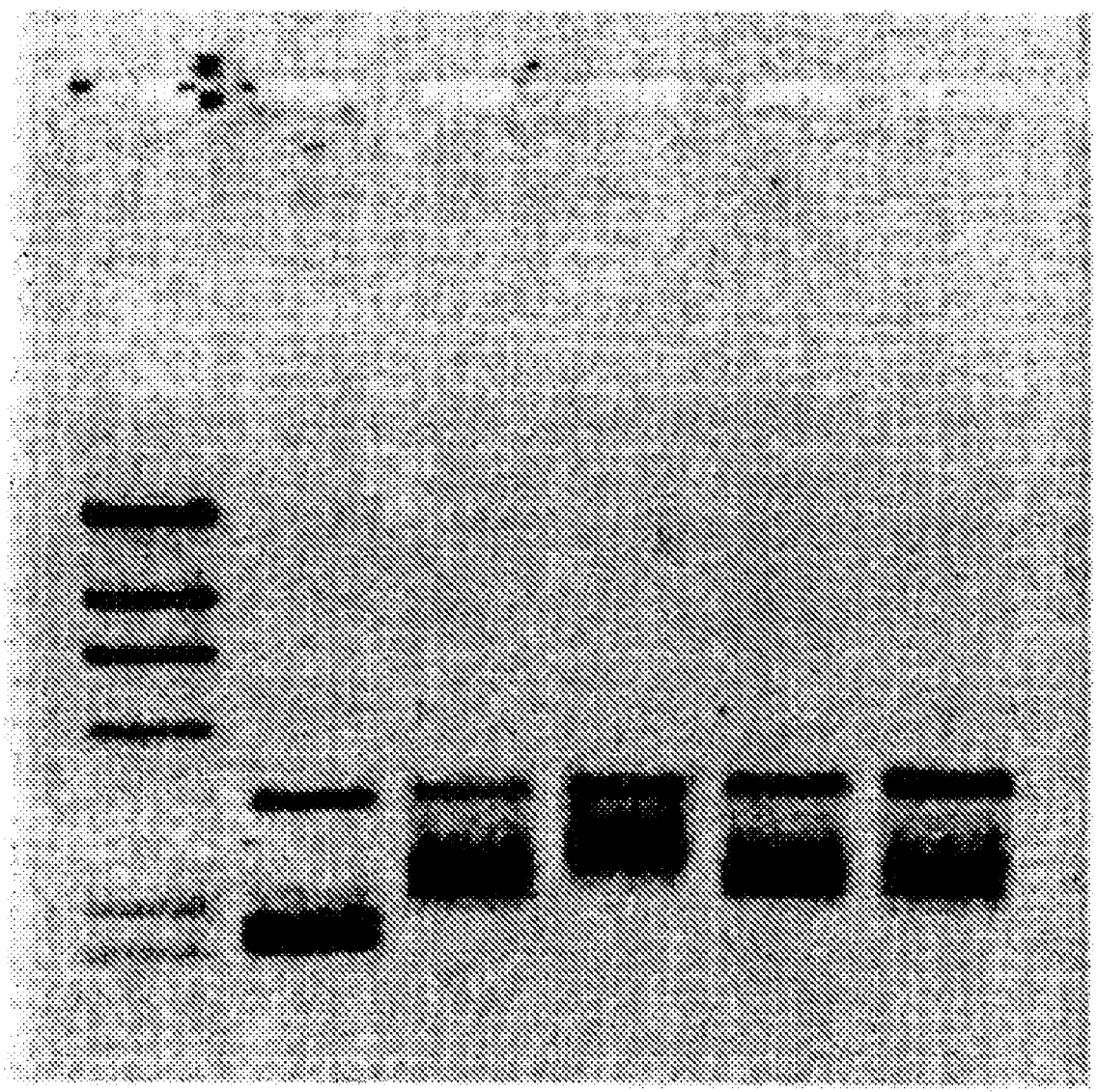
FIG. 10. DNA binding and photocleavage by [{(bpy)$_2$Os(dpp)}$_2$Ru(dpq)PtCl$_2$](PF$_6$)$_6$. Lane 1 is the molecular weight standard, lane C is the pUC18 DNA plasmid control, lane 25° is 10:1 metal complex:DNA base pair incubated at 25° C., lane 37° is the 10:1 ratio incubated at 37° C., Ar* is the 10:1 ratio photolyzed for 1 hour under Ar, lane O$_2$* is the 10:1 ratio photolyzed under ambient atmosphere.

A mixed-metal complex, [{(bpy)$_2$Os(dpp)}$_2$Ru(dpq)PtCl$_2$](PF$_6$)$_6$, was synthesized using bridging ligands dpq (2,3-bis(2-pyridyl)quinoxaline), and dpp (as described in Example 3) but using osmium as a light absorbing metal component. The complex was tested as described in Example 3 and the results are presented in FIG. 10. As can be seen, the complex was effective in binding to DNA under with and without O$_2$. However, the DNA was cleaved only when O$_2$ was present, and not in the absence of O$_2$. This illustrates this metal complex also binds to DNA and photocleaves DNA in a oxygen dependent manner.

Example 5

Use of the Compounds of the Invention to Kill Hyperproliferating Cells

Collection of Protocols for Photosensitizer In Vitro and In Vivo

Protocol: In vitro Photodynamic therapy using Photo Dynamic Compounds (PDC) drugs.

Reagents comprise Culture media depending on the cell line (RPMI 1640, DUL BECOS, and MEM F 15) and the Resazurin sodium to quantify cell survival.

Equipment required Hemocytometer, Reservoirs, 96 well flat bottom plates,

Day 1 (Seeding 96 Well Plates)

After retrieving the pellet from the cell culture flask, the cell suspension is diluted by the appropriate media followed by counting the concentration using a Hemocytometer to determine the volume of the media which contains 5000 cells
The following 96 well plates are prepared for each cell line.
  No Light and Drug (NL+D)
  Light and No Drug (L+ND)
  High Light (HL) equivalent to 10 minutes at ~1 mW/cm^2
  Low Light (LL) equivalent to 30 minutes at ~mW/cm^2
Label 5 Reservoirs by the given media names, and 5 other Reservoirs for the diluted cells.
Maintain cells for 24 hours in the incubator
From the following step, all experimental procedure have to be done in the dark room.
Day 2: Adding the Photosensitizer.
  If one has 3 different drugs or 3 different concentration of one drug: Leave 3 wells of each row Blank (these wells are used for control). In the next 3 wells pour the given amount of drug A, The third 3 wells drug B, and the fourth 3 wells drug C. This is followed by overnight incubation.
  Day 3: Light Exposure, and Spectrophotometry.
    Weight 0.0022 mg of Resazurin, pour into a 1.5 ml tube and add 1000 µl of media to the tube (this will be your Resazurin stock). Label 50 ml tubes (for different media), and add 125 µl of Resazurin stock to the 24 ml of appropriate media. Prepare one reservoir for each media. Remove the 96 well plates with the PS labelled cells from the Incubator and discard the old media. Add media from the 50 ml tube containing Resazurin in the appropriate reservoir. Divide the first 2 rows (A and B) into 3 parts, each consisting of 4 wells. Add each reservoir content to 1 part, i.e. pour the first 4 wells from first reservoir, in the next four wells from the second reservoir, and in the third four wells from the third reservoir. These are controls for media and Resazurin. The first three wells of each row will be control for media+Resazurin+cells. The other wells will be Resazurin+media+drug+cells.
  Put the HL and L+ND plates on the Light box and leave it for 30 minutes. After 10 minutes put the LL plate on the Light box and leave it for 20 minutes. Incubate all plates for 4 hours. Conduct spectrophotometer readings for Resazurin fluorescence after 4, 6, and 8 hours.
In Vivo Models
  CNS-1 Brain Tumor model.
  For CNS-1-luc implantation, Lewis rats will be anesthetized with 2.5% isofluorane –97.5% carbogen (5% CO2, 95% O2) anesthesia (1 L/min) in a clear chamber, and anesthesia will be sustained using a nose cone (1% isofluorane-99% carbogen)
  The scalp will be shaved and disinfected using betadine prior to performing a 1.5 cm incision along the midline. The skull will be carefully exposed and cleaned with saline. A 2 mm diameter burr hole will be made in the left hemisphere using a Dremel tool, 3 mm posterior to the bregma, thereby exposing the dura but leaving it intact. An injection of 300,000 CNS-1 exponential-phase cells in 5 uL of media will be performed on the left hemisphere using a 26G Hamilton syringe over a period of 5 min to avoid mechanical/pressure damage. The needle will be slowly retracted, the burr hole left open and the skin sutured closed.

After surgical procedure, saline solution (3 mL) will be administrated subcutaneously to prevent dehydration, and the animal will be returned to the cage and allowed to recover. For analgesia, 0.05 mg/kg buprenorphine will be given SQ (0.2 mL/kg BW of Temgesic 0.3 mg/mL) 4 hrs before cells implantation and repeated every 8 hours for 24 hours. The animals will be monitored continually until they are fully recovered.

Photodynamic Therapy Parameter Range to be Tested Included.
a) Time interval after tumor implantation
b) Photosensitizers:
  Drug dose
  Route of administration
  Drug-light interval
c) Light parameters
  Wavelength
  Light dose
  Light dose Rate
  Light dose: chronic or acute
  Efficacy of PS mediated PDT will be assessed by measuring the BLI intensity prior and post PDT, as well as the BLI recovery as a function of time post PDT versus untreated animals. The BLI intensity was shown to correlate with total tumour volume.
MT-1-luc Cells Injection for Metastatic Tumor Model.
  Vertebral metastases were generated by injection of human breast cancer carcinoma cells (MT-1)-luc into 5-8 week old female nude rats (mu/mu; Harlan Sprague-Dawley, Indianapolis, Ind.).
  In animals of the tumor group, 2×106 cells in 200 µL RPMI 1640 media were injected under general anesthesia (2% isofluorane/2 L O2) into the left heart ventricle using a 1 mL syringe with a 25 g needle. Pulsatile blood within the needle cone confirmed the correct position of the needle. The animals were immediately recovered and returned to their cages with free access to standard food and water.
  Fifteen days later in vivo bioluminescence imaging confirmed the establishment of metastases. For this luciferin (Xenogen Corp., Alameda, Calif.) was dissolved in 0.9% sodium chloride solution at a concentration of 30 and 60 mg kg 1 was injected intraperitoneally to anesthetized animals. Five minutes later the bioluminescent signal was acquired using an IVIS Bioluminescent Imaging system (Xenogen Corp.). Images of each rat were taken in the left lateral and ventral positions. Rats with bioluminescence-confirmed metastases were subsequently injected intravenously with photosensitizers. The animals were euthanized at specified time points according to experimental group.
  [Source: Photodynamic Therapy of Vertebral Metastases: Evaluating Tumor-to-Neural Tissue Uptake of BPD-MA and ALA-PpIX in a Murine Model of Metastatic Human Breast Carcinoma Margarete K. Aken, Albert J. M. Yee, Brian C. Wilson, Shane Burch, Crystal L. Johnson, Lothar Lilge and Stuart K. Bisland]
Photodynamic Therapy
d) Time interval after tumor implantation
e) Photosensitizers:
  Drug dose
  Route of administration Drug-light interval
f) Light parameters
   Wavelength
   Light dose
   Light dose Rate
   Light dose: chronic or acute As above the response to a particular metastases to PS mediated PDT will provide a measure for the PS efficacy While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A supramolecular complex comprising
   at least one metal to ligand charge transfer (MLCT) light absorbing metal,
   at least one bridging ligand selected from the group consisting of 2,3-bis(2-pyridyl) pyrazine,2,2'-bipyridimidine, 2,3,-bis(2-pyridyl)quinoxaline, and 2,3,5,6-tetrakis(2-pyridyl)pyrazine, and
   at least one Pt based DNA binding unit which is cis $PtCl_2$.

2. The supramolecular complex of claim 1 wherein said at least one metal to ligand charge transfer (MLCT) light absorbing metal is selected from the group consisting of ruthenium(II), osmium(III), rhenium(I), iron(II) and platinum(II).

3. The supramolecular complex of claim 1, wherein said supramolecular complex further comprises at least one terminal ligand.

4. The supramolecular complex of claim 3, wherein said at least one terminal ligand is a π-acceptor ligand.

5. The supramolecular complex of claim 3, wherein said at least one terminal ligand is selected from the group consisting of 2,2'-bipyridine; 2,2':6',2"-terpyridine; triphenylphosphine; and 2,2'-phenylpyridine and diethylphenylphosphine.

6. The supramolecular complex of claim 1, further comprising a counterion.

7. The supramolecular complex of claim 6, wherein said counterion is selected from the group consisting of $PF_6^-$, $Cl^-$, $Br^-$, $I^-$, $CF_3SO_3^-$, $BF_4^-$, $NO_3^-$, $ClO_4^-$, $CO_3^{-2}$, $SO_4^{2-}$.

8. The supramolecular complex of claim 1 wherein said supramolecular complex is selected from the group consisting of
   [{(bpy)$_2$Ru(dpp)}$_2$Ru(dpp)PtCl$_2$](PF$_6$)$_6$, [{(bpy)$_2$Ru(dpp)}$_2$Ru(dpq)PtCl$_2$](PF$_6$)$_6$, [{(bpy)$_2$Ru(dpp)}$_2$Ru(dpb)PtCl$_2$](PF$_6$)$_6$, [{(phen)$_2$Ru(dpp)}$_2$Ru(dpp)PtCl$_2$](PF$_6$)$_6$ and [{(bpy)$_2$Os(dpp)}$_2$Ru(dpq)PtCl$_2$](PF$_6$)$_6$.

9. A method for cleaving DNA comprising the steps of
   combining said DNA with a supramolecular complex comprising
      at least one metal to ligand charge transfer (MLCT) light absorbing metal,
      at least one bridging ligand selected from the group consisting of 2,3-bis(2-pyridyl)pyrazine, 2,2'-bipyridimidine, 2,3,-bis(2-pyridyl) quinoxaline, and 2,3,5,6-tetrakis(2-pyridyl)pyrazine, and
      at least one Pt based DNA binding unit which is cis $PtCl_2$,
      said combining being carried out in the presence of molecular oxygen and under conditions that allow said at least one Pt based DNA binding unit to bind to said DNA; and
   exposing said DNA to light or radiant energy in a quantity sufficient to cause sensitization of said molecular oxygen by said MLCT light absorbing metal, thereby forming a reactive oxygen species that cleaves said DNA.

10. The method of claim 9 wherein said at least one metal to ligand charge transfer (MLCT) light absorbing metal is selected from the group consisting of ruthenium(II), osmium (III), rhenium(I), iron(II) and platinum(II).

11. The method of claim 9, wherein said supramolecular complex further comprises at least one terminal ligand.

12. The supramolecular complex of claim 11, wherein said at least one terminal ligand is a π-acceptor ligand.

13. The method of claim 11, wherein said at least one terminal ligand is selected from the group consisting of 2,2'-bipyridine; 2,2':6',2"-terpyridine; triphenylphosphine; and 2,2'-phenylpyridine and diethylphenylphosphine.

14. The method of claim 9 wherein said light is visible light.

15. The method of claim 9, wherein said supramolecular complex further comprises a counterion.

16. The supramolecular complex of claim 15, wherein said counterion is selected from the group consisting of $PF_6^-$, $Cl^-$, $Br^-$, $I^-$, $CF_3SO_3^-$, $BF_4^-$, $NO_3^-$, $ClO_4^-$, $CO_3^{-2}$, $SO_4^{2-}$.

17. The method of claim 9 wherein said supramolecular complex is selected from the group consisting of [{(bpy)$_2$Ru(dpp)}$_2$Ru(dpp)PtCl$_2$](PF$_6$)$_6$, [{(bpy)$_2$Ru(dpp)}$_2$Ru(dpq)PtCl$_2$](PF$_6$)$_6$, [{(bpy)$_2$Ru(dpp)}$_2$Ru(dpb)PtCl$_2$](PF$_6$)$_6$, [{(phen)$_2$Ru(dpp)}$_2$Ru(dpp)PtCl$_2$](PF$_6$)$_6$ and [{(bpy)$_2$Os(dpp)}$_2$Ru(dpq)PtCl$_2$](PF$_6$)$_6$.

18. The method of claim 9 wherein said combining step occurs within a hyperproliferating cell.

19. A composition for effecting the cleavage of DNA in hyperproliferating cells, comprising,
   a supramolecular complex comprising
      at least one metal to ligand charge transfer (MLCT) light absorbing metal;
      at least one bridging ligand selected from the group consisting of 2,3-bis(2-pyridyl)pyrazine, 2,2'-biyridimidne, 2,3,-bis(2-pyridyl) quinoxaline, and 2,3,5,6-tetrakis(2-pyridyl)pyarzine;
      at least one Pt based DNA binding unit which is cis $PtCl_2$; and a carrier.

20. The composition of claim 19 wherein said at least one metal to ligand charge transfer (MLCT) light absorbing metal is selected from the group consisting of ruthenium(II), osmium(III), rhenium(I), iron(II) and platinum(II).

21. The composition of claim 19, wherein said supramolecular complex further comprises at least one terminal ligand.

22. The composition of claim 21, wherein said at least one terminal ligand is a π-acceptor ligand.

23. The composition of claim 21, wherein said at least one terminal ligand is selected from the group consisting of 2,2'-bipyridine; 2,2':6',2"-terpyridine; triphenylphosphine; and 2,2'-phenylpyridine and diethylphenylphosphine.

24. The composition of claim 19 further comprising a carrier, said supramolecular complex being dissolved or dispersed in said carrier.

25. The composition of claim 19, wherein said supramolecular complex further comprises a counterion.

26. The supramolecular complex of claim 25, wherein said counterion is selected from the group consisting of $PF_6^-$, $Cl^-$, $Br^-$, $I^-$, $CF_3SO_3^-$, $BF_4^-$, $NO_3^-$, $ClO_4^-$, $CO_3^{-2}$, $SO_4^{2-}$.

27. The composition of claim 19 wherein said supramolecular complex is selected from the group consisting of [{(bpy)$_2$Ru(dpp)}$_2$Ru(dpp)PtCl$_2$](PF$_6$)$_6$, [{(bpy)$_2$Ru(dpp)}$_2$Ru(dpq)PtCl$_2$](PF$_6$)$_6$, [{(bpy)$_2$Ru(dpp)}$_2$Ru(dpb)

PtCl$_2$](PF$_6$)$_6$, [{(phen)$_2$Ru(dpp)}$_2$Ru(dpp)PtCl$_2$](PF$_6$)$_6$ and [{(bpy)$_2$Os(dpp)}$_2$Ru(dpq)PtCl$_2$](PF$_6$)$_6$.

28. A method for decreasing the replication of hyperproliferating cells, comprising the steps of
delivering to said cells a supramolecular complex comprising
at least one metal to ligand charge transfer (MLCT) light absorbing metal;
at least one bridging ligand selected from the group consisting of 2,3-bis(2-pyridyl)pyrazine, 2,2'-bipyridimidine, 2,3,-bis(2-pyridyl) quinoxaline, and 2,3,5,6-tetrakis(2-pyridyl)pyrazine; and
at least one Pt based DNA binding unit which is cis PtCl$_2$; and
applying light or radiant energy to said hyperproliferating cells, wherein said step of applying light to said hyperproliferating cells induces sensitization of said molecular oxygen by said MLCT light absorbing metal, thereby forming a reactive oxygen species that cleaves said DNA of said hyperproliferating cells, thereby causing a decrease in the replication of said hyperproliferating cells.

29. The method of claim 28, wherein said at least one metal to ligand charge transfer (MLCT) light absorbing metal is selected from the group consisting of ruthenium(II), osmium (III), rhenium(I), iron(II) and platinum(II).

30. The method of claim 28, wherein said supramolecular complex further comprises at least one terminal ligand.

31. The method of claim 30, wherein said at least one terminal ligand is a π-acceptor ligand.

32. The method of claim 30, wherein said at least one terminal ligand is selected from the group consisting of 2,2'-bipyridine; 2,2':6',2''-terpyridine; triphenylphosphine; and 2,2'-phenylpyridine and diethylphenylphosphine.

33. The method of claim 28 wherein said light is visible light.

34. The method of claim 28, wherein said supramolecular complex further comprises a counterion.

35. The supramolecular complex of claim 34, wherein said counterion is selected from the group consisting of PF$_6^-$, Cl$^-$, Br$^-$, I$^-$, CF$_3$SO$_3^-$, BF$_4^-$, NO$_3^-$, CLO$_4^-$, CO$_3^{-2}$, SO$_4^{2-}$.

36. The method of claim 28 wherein said supramolecular complex is selected from the group consisting of [{(bpy)$_2$Ru(dpp)}$_2$Ru(dpp)PtCl$_2$](PF$_6$)$_6$, [{(bpy)$_2$Ru(dpp)}$_2$Ru(dpq)PtCl$_2$](PF$_6$)$_6$, [{(bpy)$_2$Ru(dpp)}$_2$Ru(dpb)PtCl$_2$](PF$_6$)$_6$, [{(phen)$_2$Ru(dpp)}$_2$Ru(dpp)PtCl$_2$](PF$_6$)$_6$ and [{(bpy)$_2$Os(dpp)}$_2$Ru(dpq)PtCl$_2$](PF$_6$)$_6$.

37. The method of claim 28 wherein said hyperproliferating cells are cancer cells.

* * * * *